United States Patent
Li et al.

(10) Patent No.: US 8,653,069 B2
(45) Date of Patent: Feb. 18, 2014

(54) ARALKYL SUBSTITUTED PIPERIDINE OR PIPERAZINE DERIVATIVES AND THEIR USE FOR TREATING SCHIZOPHRENIA

(75) Inventors: Jianqi Li, Shanghai (CN); Shaoping Peng, Shanghai (CN); Wangping Cai, Nanjing (CN); Kai Gao, Nanjing (CN)

(73) Assignee: Jiangsu Hengyi Pharmaceutical Co., Ltd., Nanjing, Jiangsu Province (CN)

( * ) Notice: Subject to any disclaimer, the term of this patent is extended or adjusted under 35 U.S.C. 154(b) by 123 days.

(21) Appl. No.: 13/056,365

(22) PCT Filed: Jul. 28, 2008

(86) PCT No.: PCT/CN2008/001385
§ 371 (c)(1),
(2), (4) Date: Mar. 9, 2011

(87) PCT Pub. No.: WO2010/012121
PCT Pub. Date: Feb. 4, 2010

(65) Prior Publication Data
US 2011/0160199 A1    Jun. 30, 2011

(51) Int. Cl.
*A61K 31/536* (2006.01)
*A61K 31/496* (2006.01)
*A61K 31/4545* (2006.01)
*C07D 413/12* (2006.01)
*C07D 413/14* (2006.01)

(52) U.S. Cl.
USPC ............. 514/230.5; 514/253.07; 514/254.04; 514/312; 544/105; 544/363; 544/368; 546/158

(58) Field of Classification Search
None
See application file for complete search history.

(56) References Cited

U.S. PATENT DOCUMENTS

| | | | |
|---|---|---|---|
| 5,147,881 A | 9/1992 | Howard, Jr. | |
| 5,350,747 A | 9/1994 | Howard | |
| 6,251,907 B1 * | 6/2001 | Strupczewski et al. | .. 514/254.04 |
| 2004/0138230 A1 | 7/2004 | Andreana et al. | |
| 2008/0113988 A1 | 5/2008 | Andres-Gil et al. | |

FOREIGN PATENT DOCUMENTS

| | | |
|---|---|---|
| CN | 1307562 | 8/2001 |
| CN | 1701072 | 11/2005 |
| CN | 101084225 | 12/2007 |
| CN | 101302214 | 11/2008 |
| WO | 92-08718 | 5/1992 |
| WO | 99-55672 | 11/1999 |

OTHER PUBLICATIONS

International Search Report and Written Opinion mailed May 7, 2009 in International Patent Application No. PCT/CN2008/001385, filed Jul. 28, 2008.
Response filed in EP Patent Office for EP08783576.5 dated Jan. 22, 2013.
Search Report for EP08783576.5 dated Mar. 22, 2012.

* cited by examiner

*Primary Examiner* — Emily Bernhardt
(74) *Attorney, Agent, or Firm* — Andrus Intellectual Property Law, LLP

(57) ABSTRACT

The present invention discloses an aralkyl substituted piperidine or piperazine derivative and the use of the derivative in preparation of medicaments for treating schizophrenia and correlative psychoneuroses. It is shown by pharmacological tests that the derivative of the present invention has better antischizophrenic effect and less toxicity. Said derivative is a free base or salt of the compound having the following general formula.

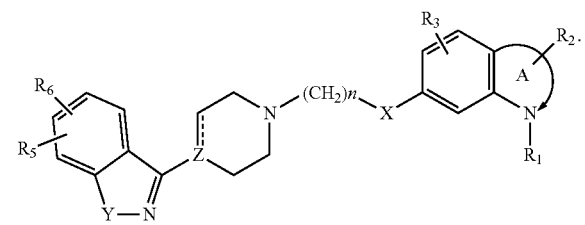

13 Claims, 2 Drawing Sheets

ARALKYL SUBSTITUTED PIPERIDINE OR PIPERAZINE DERIVATIVES AND THEIR USE FOR TREATING SCHIZOPHRENIA

CROSS-REFERENCE TO RELATED APPLICATION

This application is the U.S. national stage application of International Application PCT/CN2008/001385, filed Jul. 28, 2008, which international application was published on Feb. 4, 2010 as International Publication WO 2010/012121 in the Chinese language.

TECHNICAL FIELD

The present invention relates to an aralkyl substituted piperidine or piperazine derivative, a process for preparing thereof and use thereof.

BACKGROUND

Schizophrenia is a common serious mental illness, and is the most serious and damaging kind in all mental illness. The worldwide incidence of schizophrenia is about 1%, and has a significant increasing trend with the environmental deterioration and the increasing living pressure. Most patients with schizophrenia give up treatment due to long treatment cycle, high treatment cost and big side effects, which lead to more severe social consequences.

A large number of studies have shown that a dopamine system of the brain is closely related to human's normal mental activities. A disorder of the dopamine system can lead to a variety of psychoneuroses such as schizophrenia, neuropathic pain, mania, anxiety disorder, all kinds of depression, Parkinson's disease, etc. Of the above diseases, schizophrenia has the closest relation to dopaminergic system.

Traditional antipsychotic drugs (such as dopamine $D_2$ receptor antagonists) and non-typical antipsychotic drugs (such as $D_2$/5-HT dual antagonists) are clinically used at the moment, wherein traditional antipsychotic drugs have been eliminated gradually since they cause extrapyramidal symptoms (EPS) easily. There are many types of non-typical antipsychotic drugs, whereas none of them is prominent in improving the entire schizophrenia spectrum, and most of them only improve a syndrome in positive or negative symptoms or reduce side effects. Therefore, finding a novel anti-schizophrenia medicament having a low side effect, rapid onset of action and a broad spectrum of treatment is always a focus among the worldwide pharmaceutical industries.

In recent years, scientists have found that partial dopamine receptor agonists can reduce rather than completely block the transmission of dopamine in dopamine over-activity, while cause excitement when dopaminergic activity is low on the contrary. The partial dopamine receptor agonists have a significant treatment effect on both positive and negative symptoms of the mental illness, and reduce reoccurrence of schizophrenia and improve emotion and cognitive dysfunction if administrated in long-term use. The EPS side effect and the action of increasing a level of prolactin in serum are smaller than both traditional antipsychotic drugs and non-typical antipsychotic drugs. Therefore, a novel anti-schizophrenia medicament having a function of partial agonization of dopamine $D_2$ receptor is a focus and an important development target of the current research.

The aralkyl substituted piperidine or piperazine derivative of the present invention can stabilize the dopaminergic system of the brain, and show potential for treating and improving a variety of psychoneuroses, and can be used for the treatment of neuropathic pain, mania, schizophrenia, anxiety disorder, all kinds of depressions. Parkinson's disease, in particularly schizophrenia.

CONTENTS OF THE INVENTION

One of the technical problems to be solved by the present invention is to disclose an aralkyl substituted piperidine or piperazine derivative to overcome the defects of currently used drugs such as an obvious extrapyramidal symptom and an increased level of prolactin, and to solve clinical problems and meet clinical requirements.

The second technical problem to be solved by the present invention is to disclose use of the above compound for the preparation of a medicament for treating schizophrenia and the associated psychoneuroses.

The aralkyl substituted piperidine or piperazine derivative described in the present invention is a compound represented by the following formula (1) or a free base or a salt thereof:

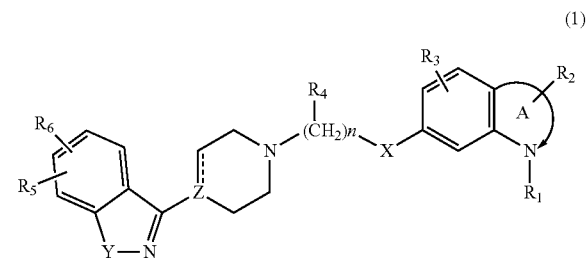

(1)

When the compound of the formula 1 is a free base, all of them can form different salts with various inorganic acids and organic acids.

The salts are those comprising pharmaceutically acceptable anions, such as hydrochloride, hydrobromide, hydriodide, nitrate, sulfate or bisulfate, phosphate or acid phosphate, acetate, lactate, citrate, tartrate, maleate, fumarate, gluconate, glucarate, benzoate, methanesulfonate, ethanesulfonate, benzenesulfonate, p-toluenesulfonate, wherein the above salts are those preferably comprising 0.5-3 molecules of crystal water, and said salt is preferably hydrochloride, hydrobromide, sulfate, trifluoroacetate or methanesulfonate.

In formula (1):

A ring is a 5-7 membered heterocycle containing a nitrogen atom, the heterocycle optionally further contains heteroatoms selected from O, S, N. A ring are presented by some of the following structures:

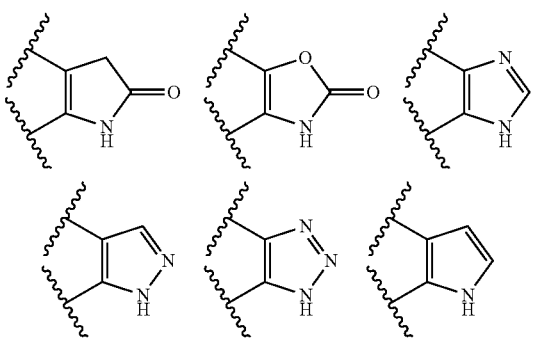

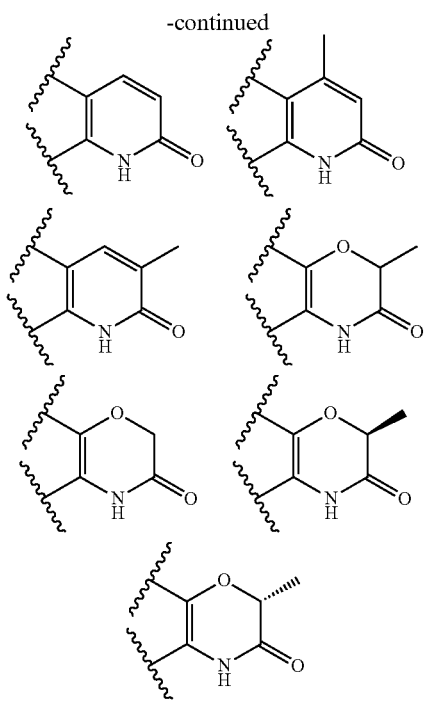

X is oxy, amino or substituted amino,

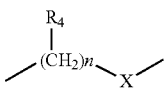

is presented by some following structures:

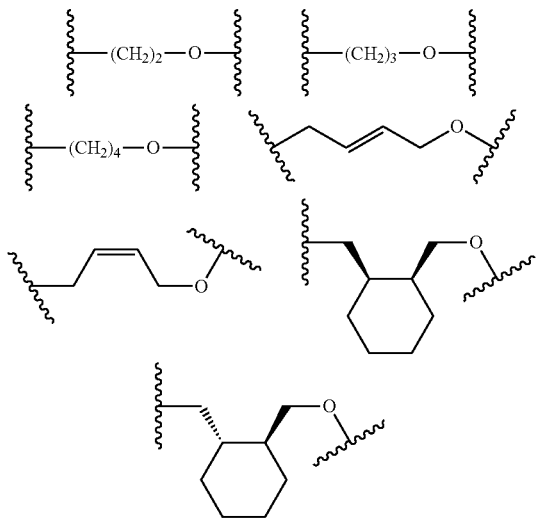

===== is a single or double bond. When ===== is a single bond, Z is CH or N; when ===== is a double bond, Z is C;

Y is O, N, or S;

n is an integer of 1-5;

$R_1$, represents hydrogen, $C_1$-$C_4$ alkyl, a $C_5$ or $C_6$ aliphatic ring, phenyl or substituted phenyl, or hydroxy;

$R_2$ represents hydrogen, $C_1$-$C_4$ alkyl, a $C_5$ or $C_6$ aliphatic ring, phenyl or substituted phenyl, hydroxy, amino or substituted amino, $C_1$-$C_4$ alkoxy, $C_1$-$C_4$ acyl, or halogen; wherein the alkyl moiety in the $C_1$-$C_4$ alkyl, $C_1$-$C_4$ alkoxy, $C_1$-$C_4$ acyl, a $C_5$ or $C_6$ aliphatic ring can be optionally substituted by 1-3 fluorine atom(s); said substituted phenyl is phenyl having 1 to 4 substituents and the substituent is halogen, hydroxy, alkoxy or amino. The substituted phenyl hereinafter described has the same meaning as defined herein:

$R_3$ is selected from the group consisting of hydrogen, halogen, $C_1$-$C_4$ alkyl, $C_1$-$C_4$ alkoxy, amino, and substituted amino, wherein the $C_1$-$C_4$ alkyl and $C_1$-$C_4$ alkoxy may contain N, S, O, F atoms, said substituted amino is amino having $C_1$-$C_4$ alkyl, a $C_5$ or $C_6$ aliphatic ring, phenyl or substituted phenyl substituents. The substituted amino hereinafter described has the same meaning as defined herein;

$R_4$ represents one of hydrogen, $C_1$-$C_4$ alkyl, a $C_5$ or $C_6$ aliphatic ring, phenyl or substituted phenyl, hydroxy, amino or substituted amino, $C_1$-$C_4$ alkoxy, $C_1$-$C_4$ acyl, halogen, carboxylic acid or carboxylic ester; wherein the alkyl moiety in $C_1$-$C_4$ alkyl, $C_1$-$C_4$ alkoxy, $C_1$-$C_4$ acyl, a $C_5$ or $C_6$ aliphatic ring may be optionally substituted by 1-3 fluorine atom(s);

$R_5$ or $R_6$ represents one of hydrogen, $C_1$-$C_4$ alkyl, a $C_5$ or $C_6$ aliphatic ring, 5- or 6-membered saturated or unsaturated aliphatic ring containing one or two N, O, S heteroatom(s), phenyl or substituted phenyl, hydroxy, $C_1$-$C_4$ alkoxy, $C_1$-$C_4$ acyl, halogen, carboxylic acid or carboxylic ester, amino or substituted amino, nitro or acetonitrile; wherein the alkyl moiety in $C_1$-$C_4$ alkyl, $C_1$-$C_4$ alkoxy, $C_1$-$C_4$ acyl or a $C_5$ or $C_6$ aliphatic ring can be optionally substituted by 1-3 fluorine atom(s).

Other preferably examples of the present invention relate to compounds of formula 1 and a pharmaceutically acceptable salt thereof, wherein when X is oxy, then Z is CH, and Y is O, N, or S.

Other preferable examples of the present invention relate to compounds of formula 1 and a pharmaceutically acceptable salt thereof, wherein when X is oxy, then Z is C, ===== is a double bond, and Y is O, N, or S.

Other preferably examples of the present invention relate to compounds of formula 1 and a pharmaceutically acceptable salt thereof, wherein when X is oxy, then Z is N, and Y is O, N, or S.

Other preferable examples of the present invention relate to compounds of formula 1 and a pharmaceutically acceptable salt thereof, wherein when X is O, then $R_3$ is Cl or —OCH$_3$.

The aralkyl substituted piperidine or piperazine derivative of the present invention is characterized in that the asymmetric carbon in the structure is an achiral or chiral carbon atom.

The aralkyl substituted piperidine or piperazine derivative of the present invention is characterized in that the salt thereof comprises a pharmaceutically acceptable anion, wherein the salt is hydrochloride, hydrobromide, sulfate, trifluoroacetate or methanesulfonate and contain 0.5-3 molecules of crystal water.

The aralkyl substituted piperidine or piperazine derivative comprises:

I-1 7-[4-(4-(3-(6-chloro-benzisoxazolyl))-1-piperazinyl)-n-butoxy]-3,4-dihydro-2(1H)-quinolinone, I-2 7-[4-(4-(3-(5-chloro-benzisoxazolyl))-1-piperazinyl)-n-butoxy]-3,4-dihydro-2(1H)-quinolinone, I-3 7-[4-(4-(3-(benzisoxazolyl))-1-piperazinyl)-n-butoxy]-3,4-dihydro-2(1H)-quinolinone, I-4 7-[4-(4-(3-(6-fluoro-benzisoxazolyl))-1-piperazinyl)-n-butoxy]-3,4-dihydro-2(1H)-quinolinone, I-5 7-[4-(4-(3-(8-trifluoromethyl-benzisoxazoly))-1-piperazinyl)-n-butoxy]-3,4-dihydro-2(1H)-quinolinone, I-6 7-[4-(4-(3-(6-methyl-benzisoxazolyl))-1-piperazinyl)-n-butoxy]-3,4-dihydro-2(1H)-quinolinone, I-7 7-[4-(4-(3-(5-methyl-benzisoxazoly))1-piperazinyl)-n-butoxy]-3,4-dihydro-2(1H)-quinolinone,
I-8 7-[4-(4-(3-(6-hydroxy-benzisoxazolyl))-1-piperazinyl)-n-butoxy]-3,4-dihydro-2(1H)-quinolinone,
I-9 7-[4-(4-(3-(5-methoxy-benzisoxazolyl))-1-piperazinyl)-n-butoxy]-3,4-dihydro-2(1H)-quinolinone,
I-10 7-[4-(4-(3-(5-cyano-benzisoxazolyl))-1-piperazinyl)-n-butoxy]-3,4-dihydro-2(1H)-quinolinone,
I-11 7-[4-(4-(3-(5-bromo-benzisoxazoly))1-piperazinyl)-n-butoxy]-3,4-dihydro-2(1H)-quinolinone,
I-12 7-[4-(4-(3-(7-bromo-6-methoxy-benzisoxazolyl))-1-piperazinyl)-n-butoxy]-3,4-dihydro-2(1H)-quinolinone,
II-1 7-[4-(4-(3-(8-fluoro-benzisoxazolyl))-1-piperidinyl)-n-butoxy]-3,4-dihydro-2(1H)-quinolinone,
II-2 7-[3-(4-(3-(6-fluoro-benzisoxazolyl))-1-piperidinyl)-n-propoxy]-3,4-dihydro-2(1H)-quinolinone,
II-3 7-[2-(4-(3-(6-fluoro-benzisoxazolyl))-1-piperidinyl)-ethoxy]-3,4-dihydro-2(1H)-quinolinone,
II-4 7-[2-(4-(3-benzisoxazolyl)-1-piperidinyl)-ethoxy]-3,4-dihydro-2(1H)-quinolinone,
II-5 7-[4-(4-(3-(6-chloro-benzisoxazolyl))-1-piperidinyl)-n-butoxy]-3,4-dihydro-2(1H)-quinolinone,
II-6 7-[4-(4-(3-(5-methoxy-benzisoxazolyl))-1-piperidinyl)-n-butoxy]-3,4-dihydro-2(1H)-quinolinone,
II-7 7-[4-(4-(3-(5-fluoro-benzisoxazoly))-1-piperidinyl)-n-butoxy]-3,4-dihydro-2(1H)-quinolinone,
II-8 7-[4-(4-(3-(5,6-dimethoxy-benzisoxazolyl))1-piperidinyl)-n-butoxy]-3,4-dihydro-2(1H)-quinolinone,
II-9 7-[4-(4-(3-(5-hydroxy-benzisoxazolyl))-1-piperidinyl)-n-butoxy]-3,4-dihydro-2(1H)-quinolinone,
II-10 7-[4-(4-(3-(5,8-dihydroxy-benzisoxazolyl))-1-piperidinyl)-n-butoxy]-3,4-dihydro-2(1H)-quinolinone,
II-11 E-7-[4-(4-(3-(6-fluoro-benzisoxazoly))1-piperidinyl)-2-butenyloxy]-3,4-dihydro-2(1H)-quinolinone,
II-12 Z-7-[4-(4-(3-(6-fluoro-benzisoxazolyl))-1-piperidinyl)-2-butenyloxy]-3,4-dihydro-2(1H)-quinolinone,
II-13 7-(((1R,2S)-2-(4-(3-(6-fluoro-benzisoxazolyl))-1-piperidinyl)methyl)cyclohexyl)methoxy)-3,4-dihydro-2(1H)-quinolinone,
II-14 7-(((1R,2R)-2-(4-(3-(8-fluoro-benzisoxazoly))-1-piperidinyl)methyl)cyclohexyl)methoxy)-3,4-dihydro-2(1H)-quinolinone,
III-1 7-[4-(4-(3-(1,2-benzisothiazolyl))-1-piperazinyl)-n-butoxy]-3,4-dihydro-2(1H)-quinolinone,
III-2 7-[3-(4-(3-(1,2-benzisothiazolyl))-1-piperazinyl)-n-propoxy]-3,4-dihydro-2(1H)-quinolinone,
III-3 7-[2-(4-(3-(1,2-benzisothiazolyl))-1-piperazinyl)-ethoxy]-3,4-dihydro-2(1H)-quinolinone,
III-4 7-[4-(4-(3-(6-methoxy-1,2-benzisothiazolyl))-1-piperazinyl)-n-butoxy]-3,4-dihydro-2(1H)-quinolinone,
III-5 7-[4-(4-(3-(7-methoxy-1,2-benzisothiazolyl))-1-piperazinyl)-n-butoxy]-3,4-dihydro-2(1H)-quinolinone,
III-6 7-[4-(4-(3-(5-methoxy-1,2-benzisothiazolyl))-1-piperazinyl)-n-butoxy]-3,4-dihydro-2(1H)-quinolinone,
III-7 7-[4-(4-(3-(4-methoxy-1,2-benzisothiazolyl))-1-piperazinyl)-n-butoxy]-3,4-dihydro-2(1H)-quinolinone,
IV-1 6-(4-(4-(3-(6-fluoro-benzisoxazolyl))-1-piperidinyl)-n-butoxy)-indoline-2-one,
IV-2 5-(4-(4-(3-(6-fluoro-benzisoxazolyl))-1-piperidinyl)-n-butoxy)-2(3H)-benzoxazolone,
IV-3 6-[4-(4-(3-(6-fluoro-benzisoxazolyl-1-piperazinyl)-n-butoxy)-(1H)-indole,
IV-4 6-[4-(4-(3-(6-fluoro-benzisoxazoly))-1-piperazinyl)-n-butoxy]-(1H)-benzimidazole,
IV-5 6-[4-(4-(3-(6-fluoro-benzisoxazoly))-1-piperazinyl)-n-butoxy]-(1H)-indazole,
IV-6 6-[4-(4-(3-(6-fluoro-benzisoxazoly))-1-piperazinyl)-n-butoxy]-(1H)-benzo(1,2,3)triazole,
IV-7 7-[4-(4-(3-(6-fluoro-benzisoxazoly))-1-piperidinyl)-n-butoxy)-2(1H)-quinolinone,
IV-8 7-[4-(4-(3-(6-fluoro-benzisoxazoly))-1-piperidinyl)-n-butoxy)-2H-benzo[b][1,4]oxazine-3(4H)-one,
IV-9 7-[4-(4-(3-(6-fluoro-benzisoxazolyl))-1-piperidinyl)-n-butoxy)-3-methyl-2(1H)-quinolinone, or
IV-10 7-[4-(4-(3-(6-fluoro-benzisoxazolyl))-1-piperidinyl)-n-butoxy)-4-methyl-2(1H)-quinolinone.

The present invention also relates to a composition for treating schizophrenia comprising a therapeutically effective amount of the compound represented by formula (1) or a free base or a salt thereof and a pharmaceutically acceptable carrier.

The present invention further relates to use of the compound or a free base or a salt thereof for the preparation of a medicament for treating schizophrenia and other psychoneuroses. The psychoneuroses comprise neuropathic pain, mania, schizophrenia, anxiety disorder, all kinds of depression, Parkinson's disease, etc.

The specific structures are shown in Table 1:

TABLE 1

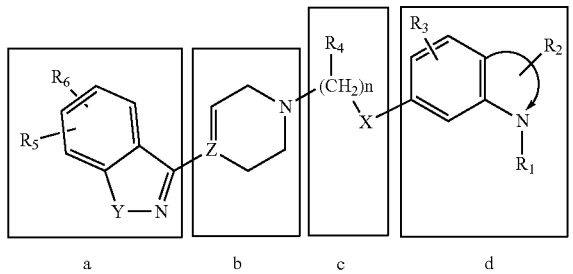

| No | a | b | c | d |
|---|---|---|---|---|
| I-1 | | | —(CH$_2$)$_4$—O— | |

TABLE 1-continued

| No | a | b | c | d |
|---|---|---|---|---|
| I-2 | 5-chloro-1,2-benzisoxazol-3-yl | piperazine | -(CH₂)₄-O- | 7-(3,4-dihydroquinolin-2(1H)-one) |
| I-3 | 1,2-benzisoxazol-3-yl | piperazine | -(CH₂)₄-O- | 7-(3,4-dihydroquinolin-2(1H)-one) |
| I-4 | 6-fluoro-1,2-benzisoxazol-3-yl | piperazine | -(CH₂)₄-O- | 7-(3,4-dihydroquinolin-2(1H)-one) |
| I-5 | 6-trifluoromethyl-1,2-benzisoxazol-3-yl | piperazine | -(CH₂)₄-O- | 7-(3,4-dihydroquinolin-2(1H)-one) |
| I-6 | 6-methyl-1,2-benzisoxazol-3-yl | piperazine | -(CH₂)₄-O- | 7-(3,4-dihydroquinolin-2(1H)-one) |
| I-7 | 6-hydroxy-1,2-benzisoxazol-3-yl | piperazine | -(CH₂)₄-O- | 7-(3,4-dihydroquinolin-2(1H)-one) |
| I-8 | 5-methyl-1,2-benzisoxazol-3-yl | piperazine | -(CH₂)₄-O- | 7-(3,4-dihydroquinolin-2(1H)-one) |
| I-9 | 5-methoxy-1,2-benzisoxazol-3-yl | piperazine | -(CH₂)₄-O- | 7-(3,4-dihydroquinolin-2(1H)-one) |

TABLE 1-continued

| No | a | b | c | d |
|----|---|---|---|---|
| I-10 | 5-cyano-1,2-benzisoxazol-3-yl | piperazine | -(CH₂)₄-O- | 3,4-dihydroquinolin-2(1H)-one-7-yl |
| I-11 | 5-bromo-1,2-benzisoxazol-3-yl | piperazine | -(CH₂)₄-O- | 3,4-dihydroquinolin-2(1H)-one-7-yl |
| I-12 | 7-bromo-6-methoxy-1,2-benzisoxazol-3-yl | piperazine | -(CH₂)₄-O- | 3,4-dihydroquinolin-2(1H)-one-7-yl |
| II-1 | 6-fluoro-1,2-benzisoxazol-3-yl | piperidine | -(CH₂)₄-O- | 3,4-dihydroquinolin-2(1H)-one-7-yl |
| II-2 | 6-fluoro-1,2-benzisoxazol-3-yl | piperidine | -(CH₂)₃-O- | 3,4-dihydroquinolin-2(1H)-one-7-yl |
| II-3 | 6-fluoro-1,2-benzisoxazol-3-yl | piperidine | -(CH₂)₅-O- | 3,4-dihydroquinolin-2(1H)-one-7-yl |
| II-4 | 1,2-benzisoxazol-3-yl | piperidine | -(CH₂)₄-O- | 3,4-dihydroquinolin-2(1H)-one-7-yl |
| II-5 | 6-chloro-1,2-benzisoxazol-3-yl | piperidine | -(CH₂)₄-O- | 3,4-dihydroquinolin-2(1H)-one-7-yl |

TABLE 1-continued
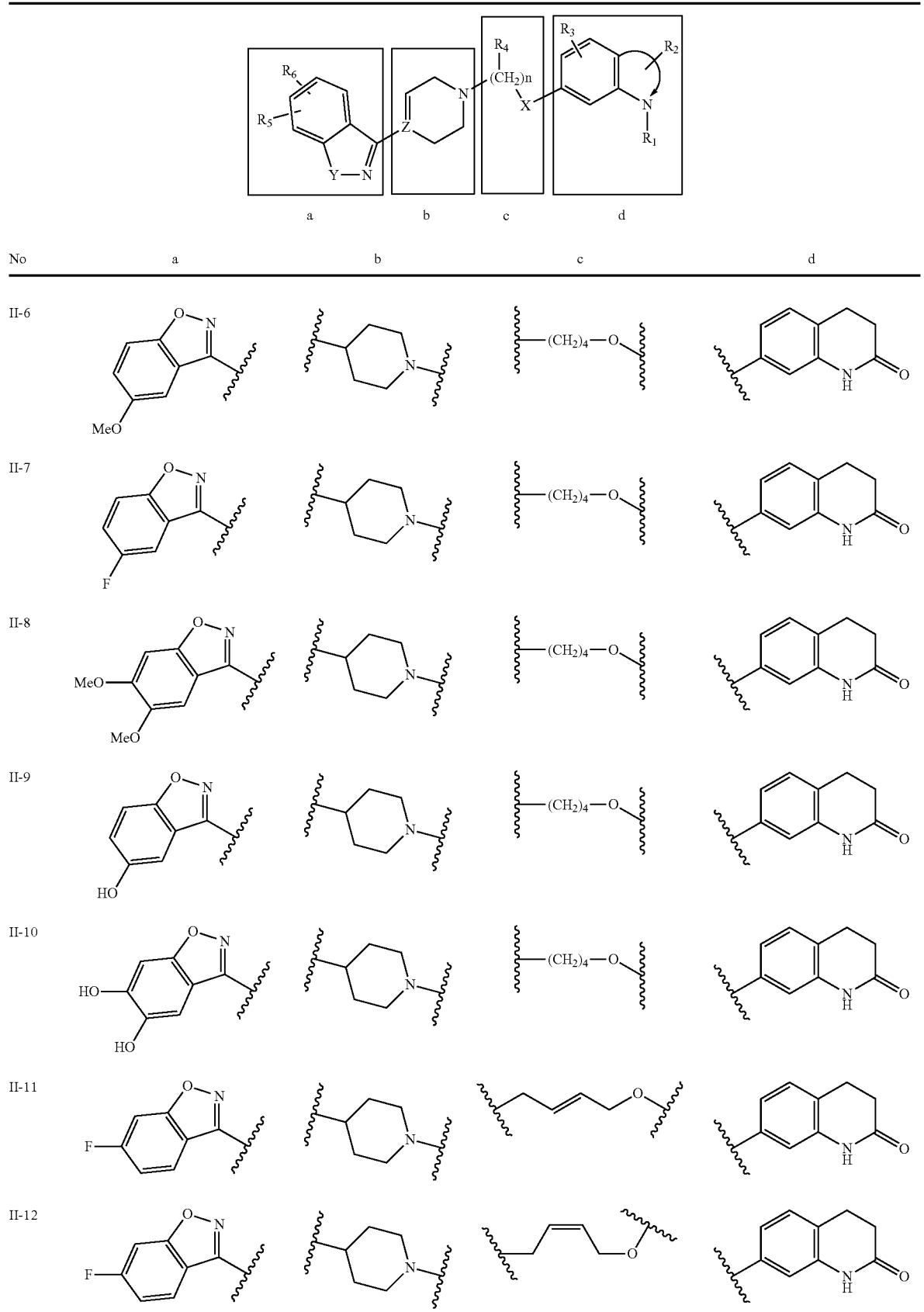

TABLE 1-continued

| No | a | b | c | d |
|---|---|---|---|---|
| II-13 | 6-fluoro-benzo[d]isoxazol-3-yl | piperidin-4-yl | -CH2-(cyclohexane-1,2-diyl)-CH2-O- | 3,4-dihydroquinolin-2(1H)-on-7-yl |
| II-14 | 6-fluoro-benzo[d]isoxazol-3-yl | piperidin-4-yl | -CH=(cyclohexylidene)-CH2-O- | 3,4-dihydroquinolin-2(1H)-on-7-yl |
| III-1 | 3-methyl-benzo[d]isothiazol-yl | piperazin-1-yl | -(CH2)4-O- | 3,4-dihydroquinolin-2(1H)-on-7-yl |
| III-2 | 3-methyl-benzo[d]isothiazol-yl | piperazin-1-yl | -(CH2)3-O- | 3,4-dihydroquinolin-2(1H)-on-7-yl |
| III-3 | 3-methyl-benzo[d]isothiazol-yl | piperazin-1-yl | -(CH2)2-O- | 3,4-dihydroquinolin-2(1H)-on-7-yl |
| III-4 | 6-MeO-benzo[d]isothiazol-3-yl | piperazin-1-yl | -(CH2)4-O- | 3,4-dihydroquinolin-2(1H)-on-7-yl |
| III-5 | 7-MeO-benzo[d]isothiazol-3-yl | piperazin-1-yl | -(CH2)4-O- | 3,4-dihydroquinolin-2(1H)-on-7-yl |
| III-6 | 5-MeO-benzo[d]isothiazol-3-yl | piperazin-1-yl | -(CH2)4-O- | 3,4-dihydroquinolin-2(1H)-on-7-yl |

US 8,653,069 B2
15  16
TABLE 1-continued
| No | a | b | c | d |
|---|---|---|---|---|
| III-7 | 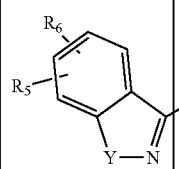 | 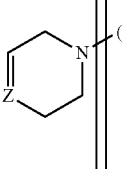 | —(CH$_2$)$_4$—O— | 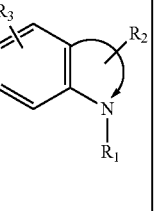 |
| IV-1 | 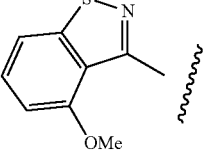 | 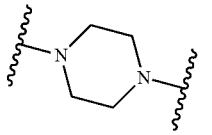 [SMILES: *N1CCN(*)CC1] | —(CH$_2$)$_3$—O— | 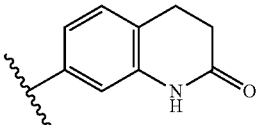 [SMILES: *c1ccc2c(c1)NC(=O)CC2] |
| IV-2 | 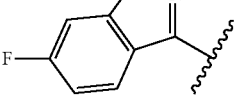 | 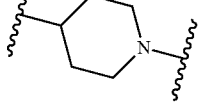 | —(CH$_2$)$_3$—O— | 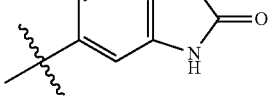 |
| IV-3 | 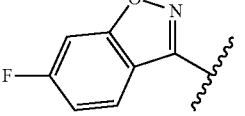 | 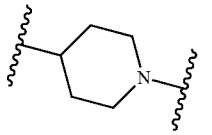 [SMILES: *C1CCN(*)CC1] | —(CH$_2$)$_3$—O— | 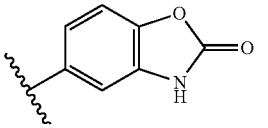 [SMILES: *c1ccc2oc(=O)[nH]c2c1] |
| IV-4 | 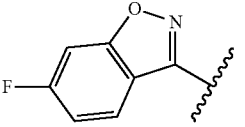 [SMILES: *c1noc2cc(F)ccc12] | 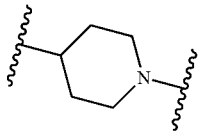 [SMILES: *C1CCN(*)CC1] | —(CH$_2$)$_3$—O— | 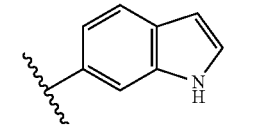 [SMILES: *c1ccc2cc[nH]c2c1] |
| IV-5 | 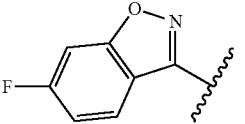 [SMILES: *c1noc2cc(F)ccc12] | 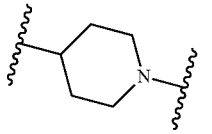 [SMILES: *C1CCN(*)CC1] | —(CH$_2$)$_3$—O— | 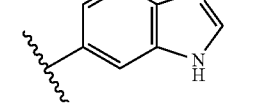 |
| IV-6 | 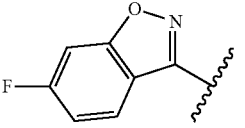 [SMILES: *c1noc2cc(F)ccc12] | 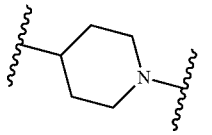 [SMILES: *C1CCN(*)CC1] | —(CH$_2$)$_3$—O— | 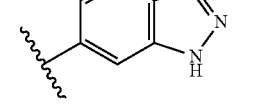 |
| IV-7 | 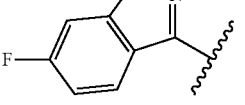 | 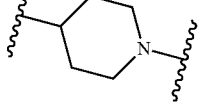 | —(CH$_2$)$_3$—O— | 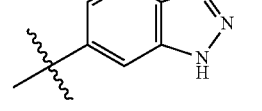 |

TABLE 1-continued

| No | a | b | c | d |
|---|---|---|---|---|
| IV-8 | 6-fluoro-1,2-benzisoxazol-3-yl | piperidine | —(CH₂)₃—O— | 6-(3-oxo-3,4-dihydro-2H-1,4-benzoxazin-6-yl) |
| IV-9 | 6-fluoro-1,2-benzisoxazol-3-yl | piperidine | —(CH₂)₃—O— | 3-methyl-2-oxo-1,2-dihydroquinolin-7-yl |
| IV-10 | 6-fluoro-1,2-benzisoxazol-3-yl | piperidine | —(CH₂)₃—O— | 4-methyl-2-oxo-1,2-dihydroquinolin-7-yl |

Wherein, further preferable compounds comprise:

II-1 7-[4-(4-(3-(6-fluoro-benzisoxazolyl))-1-piperidinyl)-n-butoxy]-3,4-dihydro-2(1H)-quinolinone, or III-1 7-[4-(4-(3-(1,2-benzisothiazolyl))-1-piperazinyl)-n-butoxy]-3,4-dihydro-2(1H)-quinolinone.

The compound of formula 1 may have a chiral center. Various isomers derived from the chiral center can be prepared through conventional methods such as resolution, fractional crystallization, or chiral synthesis, etc. A single isomer may have better activity and less side effects than its racemate.

The compound of the present invention can by prepared by the following methods:

Method 1:

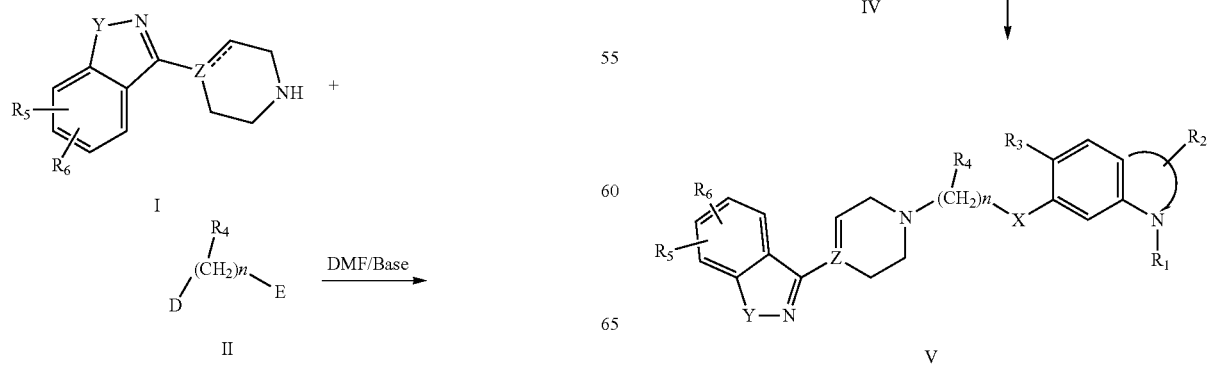

wherein D and E represent halogen: A, X, Y, Z, n, $R_1$, $R_2$, $R_3$, $R_4$, $R_5$, and $R_6$ are as described above; Base can be a organic or inorganic base such as $K_2CO_3$, $Et_3N$ or pyridine.

Compound I (10 mmol), compound II (20 mmol) and anhydrous potassium carbonate (30 mmol) are added to 30 ml of DMF. A reaction is carried out at 60° C. for 12 hours and then terminated. 100 ml of water is added to the reaction solution and the mixture is extracted with ethyl acetate (50 ml×3). The ethyl acetate extracts are combined, backwashed with 100 ml of water, washed with saturated saline, dried over anhydrous magnesium sulfate, and evaporated to dryness to obtain a white powder. The whiter powder is suspended in 30 ml of hexane, stirred for 20 minutes and filtered to obtain compound III.

Compound III (10 mmol), compound IV (20 mmol) and anhydrous potassium carbonate (30 mmol) are added to 30 ml of DMF. A reaction is carried out at 80° C. for 5 hours and then terminated. 100 ml of water is added to the reaction solution and the mixture is extracted with ethyl acetate (50 ml×3). The ethyl acetate extracts are combined, backwashed with 100 ml of water, washed with saturated saline, dried over anhydrous magnesium sulfate, and evaporated to dryness to obtain a oil, which is converted to a salt with HCl. The salt is recrystallized in ethanol (or methanol) to obtain product V.

The above compound I may be commercially available, or prepared according the method recorded in document J. Med. Chem. 1991, 34, 3316-3328 and PCT patent WO2005019215.

The above compound II may be commercially available or synthesized according to the following method:

Part of the above compound III may be commercially available. The relevant intermediate that is not commercially available easily can be prepared by a general synthesis method.

The above compound IV can be prepared by a general synthesis method.

An in vitro receptor binding assay has shown that the heterocyclic substituted piperidine or piperazine derivatives of the present invention have high affinity for dopamine $D_2$ receptor. Most of the compounds show antagonistic activity against dopamine $D_2$ receptor, and some of the compounds exhibit partial agonistic activity on dopamine $D_2$ receptor.

Results of the animal tests have shown that this type of compounds can improve relevant symptoms of a mouse models induced by apomorphine. Since these in vitro acting targets and in vivo pharmacological models are closely related to nervous system disorders caused by dopamine dysfunction, in particular schizophrenia, it suggests the treatment effect of the compound of the present invention to schizophrenia.

Results of studies on animal models have shown that the preferable compound II-1 has a remarkable anti-schizophrenia effect, a good oral absorption, an acute toxicity ($LD_{50}$>2000 mg/Kg, the mice receiving a single oral gavage dose) comparable to that of aripiprazole and ziprasidone but far less than that of risperidone. Ames-test negative, and a larger therapeutic index, which has the potential to be developed as a novel anti-schizophrenia medicament.

The derivative of the present invention may be applied to a patient in need of the treatment in form of a composition through oral administration, injection, etc., depending on conditions, ages and gender of the subject.

The composition comprises a therapeutically effective amount of said aralkyl substituted piperidine or piperazine derivative and a pharmaceutically acceptable carrier.

Said carrier is a conventional carrier commonly used in medical field, such as: diluents, excipients such as water, etc.; binders such as cellulose derivatives, gelatin, polyvinylpyrrolidone, etc.; fillers such as starch, etc.; disintegrates such as calcium carbonate, sodium bicarbonate; lubricants such as calcium stearate or magnesium stearate, etc. In addition, other adjuvants such as flavors and sweeteners can be added into the composition. The composition can be formulated to a conventional solid formulation such as tablets, powder or capsules when for oral administration, and can be formulated to injections when for injection.

Various dosage forms of the composition of the present invention can be prepared through conventional methods in the medical field, wherein the amount of the active ingredient is between 0.1% and 99.5% (weight ratio).

To sum up, the aralkyl substituted piperidine or piperazine derivative of the present invention has higher affinity for dopamine $D_2$ receptor, and not only has stronger antagonistic activity against dopamine $D_2$ receptor, but also exhibits partial agonistic activity on dopamine $D_2$ receptor. The in vivo tests have shown that this type of compounds can improve relevant symptoms of a mouse model induced by apomorphine. Since these in vitro acting targets and in vivo pharmacological models are closely related to schizophrenia, it suggests that the compound of the present invention has a treatment effect on schizophrenia. Among those compounds, II-1 has a very strong anti-schizophrenia effect, a good oral absorption, an acute toxicity ($LD_{50}$>2000 mg/Kg, the mice receiving a single oral gavage dose) comparable to that of aripiprazole and ziprasidone but far less than that of risperidone, and thus has the potential to be developed as a novel anti-schizophrenia medicament.

MODE OF CARRYING OUT THE INVENTION

Example 1

Figure 1:
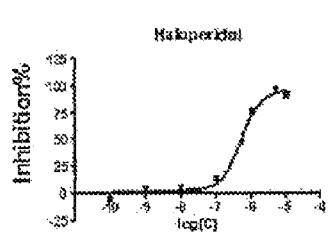
FIG. 1 represents a curve demonstrating an affinity of positive drug haloperidol for dopamine $D_2$ receptor.

I-1 7-[4-(4-(6-chloro-benzisoxazolyl)-1-piperazinyl)-n-butoxy]-3,4-dihydro-2(1H)-quinolinone hydrochloride 1) Preparation of methyl 4-chloro-salicylate 5 ml of concentrated sulfuric acid is drop-added slowly to 100 ml of methanol. The solution is cooled and then added with a powder of 4-chloro-salicylic acid (17.20 g, 0.1 mol), and a reaction is carried out at reflux for 24 hours. After cooling the reaction, a large amount of deposit precipitates and is filtered out, washed with small amount of methanol, and recrystallized in anhydrous ethanol, to obtain 15.60 g of methyl 4-chloro-salicylate, with a yield of 83%.

2) Preparation of 4-chloro-N,2-dihydroxy-benzamide

Hydroxylamine hydrochloride in solid (5.25 g, 75 mmol) is placed in an egg type flask and dissolved by drop-adding small amount of water in ice-bath. Thereafter, thereto is drop-added 15 ml of 50% NaOH solution. The reaction is stirred for 5 minutes and is drop-added 50 ml of dioxane solution of methyl 4-chloro-salicylate (9.3 g, 50 mmol) under coverage of $N_2$. After completion of drop-addition, a reaction is carried out at room temperature for 24 hours, and then a red-brown deposit precipitates, which is filtered out and placed in an egg type flask, thereto is added 50 ml of 10% hydrochloric acid and then reflux for 0.5 hour. After cooling to room temperature, a yellow deposit precipitates, which is filtered out and recrystallized in anhydrous ethanol, to obtain 8.25 g of 4-chloro-N,2-dihydroxy-benzamide, with a yield of 88%.

3) Preparation of 3-hydroxy-6-chloro-benzisoxazole 4-chloro-N,2-dihydroxy-benzamide (8 g, 42.7 mmol) is added to 10 ml of tetrahydrofuran under coverage of $N_2$, while maintaining the temperature inside vessel lower than 30° C. and thereto is drop-added slowly 10 ml of $SOCl_2$. After completion of drop-addition, the reaction is stirred for 30 minutes and evaporated to dryness. The residual SOCl2 is removed by azeotropic distillation with anhydrous benzene. The reaction is evaporated to dryness to obtain a yellow powder, which is dissolved in 10 ml of dioxane, while maintaining the temperature inside vessel at lower than 30° C., and thereto is drop-added slowly 5 ml of $Et_3N$ and stirred for 30 minutes, then thereto is drop-added 10% hydrochloric acid to pH=2. Under stirred, a large amount of light yellow deposit precipitates and is filtered out and recrystallized in methanol to obtain 6.50 g of 3-hydroxy-6-chloro-benzisoxazole, with a yield of 89%.

4) Preparation of 3,6-dichlorobenzisoxazole 3-hydroxy-6-chloro-benzisoxazole (6 g. 35 mmol). 20 ml of phosphorus oxychloride, and 1 ml of $Et_3N$ are placed in a microwave reactor. A reaction is carried out at 150° C. for 0.5 hour and is evaporated to remove phosphorus oxychloride. The residue is diluted with 20 ml of dichloromethane, and thereto is added 20 g of an ice-water mixture. The mixture is stirred and the organic phase is separated. The aqueous phase is extracted successively with dichloromethane (20 ml×2) and the dichloromethane layer is combined, washed with 20 ml of saturated saline, dried over anhydrous $MgSO_4$, evaporated to dryness, and subjected to a separation on a column of alumina (200-300 mesh), eluting with dichloromethane:methanol-200:1, to obtain 5.2 g of 3,6-dichlorobenzisoxazole, with a yield of 79%.

5) Preparation 6-chloro-3-piperazinyl-benzisoxazole 3,6-dichlorobenzisoxazole (5.2 g, 27.8 mmol), and anhydrous piperazine (24 g, 278 mmol) are placed in an egg type flask and react at 120° C. for 24 hours. After completion of the reaction, 52 ml of an ice-water mixture is added for quenching the reaction. Further 15 ml of 50% NaOH solution is added to the reaction solution. The reaction solution is stirred for 5 minutes and extracted with dichloromethane (30 ml×3). The dichloromethane layer is combined, washed with 20 ml of saturated saline, dried over anhydrous $MgSO_4$, evaporated to dryness, and subjected to a separation on a column of alumina (200-300 mesh), eluting with dichloromethane:methanol-100:1, to obtain 4.7 g of 6-chloro-3-piperazinyl-benzisoxazole, with a yield of 71%.

6) Preparation of 7-(4-chlorobutoxy)-3,4-dihydro-2(1H)-quinolinone 1-bromo-4-chloro-butane (3.4 g, 20 mmol), anhydrous potassium carbonate powder (4.14 g, 30 mmol) and 7-hydroxy-3,4-dihydro-2(1H)-quinolinone (1.63 g, 10 mmol) are added to 10 ml of acetone and reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness, to obtain a light yellow powder. The resulting powder is slurried with n-hexane (20 ml×3), filtered, and dried to obtain 1.98 g of 7-(4-chlorobutoxy)-3,4-dihydro-2(1H)-quinolinone, with a yield of 78%.

7) Preparation of 7-[4-(4-(6-chloro-benzisoxazolyl)-1-piperazinyl)-n-butoxy]-3,4-dihydro-2(1H)-quinolinone hydrochloride 7-(4-chlorobutoxy)-3,4-dihydro-2(1H)-quinolinone (278 mg, 1.1 mmol).
6-chloro-3-piperazinyl-benzisoxazole (237 mg, 1 mmol), and anhydrous potassium carbonate powder (414 mg, 3.3 mmol) are added to 10 ml of DMF and react at reflux for 24 hours. The reaction solution is evaporated to dryness, thereto is added 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder. The powder is dissolved with 5 ml of acetone and stirred in an ice bath. A white solid precipitates and is filtered, washed with small amount of acetone, and dried to obtain 260 mg of 7-[4-(4-(6-chloro-benzisoxazolyl)-1-piperazinyl)-n-butoxy]-3,4-dihydro-2(1H)-quinolinone, which is dissolved in 5 ml of anhydrous ethanol, and adjusted to pH=2 with $HCl/C_2H_5OH$, then a white solid precipitates and is filtered out and recrystallized in anhydrous ethanol, to obtain 200 mg of a product, with a yield of 38%.

Element analysis: $C_{24}H_{27}ClN_4O_3 \cdot 2HCl$ (calculated value %: C, 63.36; H, 5.98; N, 12.31. found value %: C, 63.11; H, 5.89; N, 12.01).

$^1$HNMR (DMSO-$d_6$): δ9.82 (s, 1H, CONH), 7.94-6.48 (6H, aromatic ring-H), 4.09-4.10 (2H, piperazine-H), 3.83 (t, J=6.4 Hz, 2H, O—$CH_2$,) 3.56-3.60 (2H, piperazine-H), 3.21-3.48 (m, 6H), 2.76 (t, J=8 Hz, 2H) 2.55 (t, J=8 Hz, 2H) 1.60-1.93 (m, 4H)

MS: m/z 454

Example 2

I-2 7-[4-(4-(5-chloro-benzisoxazolyl)-1-piperazinyl)-n-butoxy]-3,4-dihydro-2(1H)-quinolinone hydrochloride 5-chloro-salicylic acid is used as a starting material to replace 4-chloro-salicylic acid used in the preparation of compound I-1, to prepare the target compound through the synthesizing process in Example 1.

Element analysis: $C_{24}H_{27}ClN_4O_3 \cdot 2HCl$ (calculated value %: C, 63.36; H, 5.98; N, 12.31. found value %: C, 63.32; H, 5.92; N, 12.24).

$^1$HNMR (DMSO-$d_6$): δ10.03 (s, 1H, CONH), 7.99-6.46 (6H, aromatic ring-H), 4.10-4.15 (2H, piperazine-H), 3.99 (t, J=6.4 Hz, 2H, O—CH$_2$), 3.50-3.70 (2H, piperazine-H), 3.22-3.57 (m, 6H), 2.75 (t, J=8 Hz, 2H), 2.45 (t, J=8 Hz, 2H), 1.71-1.98 (m, 4H)

MS: m/z 454

Example 3

I-3 7-[4-(4-(benzisoxazolyl)-1-piperazinyl)-n-butoxy]-3,4-dihydro-2(1H)-quinolinone hydrochloride Salicylic acid is used as a starting material to replace the methyl 4-chloro-salicylate used in the preparation of compound I-1, to prepare the target compound through the synthesizing process in Example 1.

Element analysis: $C_{24}H_{28}N_4O_3 \cdot 2HCl$ (calculated value %: C, 68.55; H, 6.71; N, 13.32. found value %: C, 88.50; H, 6.65; N, 13.21).

$^1$HNMR (DMSO-$d_6$): δ10.00 (s, 1H, CONH), 7.96-6.48, (7H, aromatic ring-H), 4.05-4.10 (2H, piperazine-H), 3.93 (t, J=6.4 Hz, 2H, O—CH$_2$), 3.59-3.62 (2H, piperazine-H), 3.20-3.50 (m, 6H), 2.78 (t, J=8 Hz, 2H) 2.41 (t, J=8 Hz, 2H) 1.73-1.93 (m, 4H)

MS: m/z 420

Example 4

I-4 7-[4-(4-(6-fluoro-benzisoxazolyl)-1-piperazinyl)-n-butoxy]-3,4-dihydro-2(1H)-quinolinone hydrochloride 4-fluoro-salicylic acid is used as a starting material to replace the 4-chloro-salicylic acid used in the preparation of compound I-1, to prepared the target compound through the synthesizing process in Example 1.

Element analysis: $C_{24}H_{27}FN_4O_3 \cdot 2HCl$ (calculated value %: C, 56.36; H, 5.72; N, 10.96. found value %: C, 56.49; H, 5.75; N, 10.88).

$^1$HNMR (DMSO-$d_6$): δ10.08 (s, 1H, CONH), 8.02-6.48, (6H, aromatic ring-H), 4.01-4.11 (2H, piperazine-H), 3.97 (t, J=6.4 Hz, 2H, O—CH$_2$), 3.57-3.64 (2H, piperazine-H), 3.22-3.48 (m, 6H), 2.79 (t, J=8 Hz, 2H), 2.40 (t, J=8 Hz, 2H) 1.80-1.93 (m, 4H)

MS: m/z 438

Example 5

I-5 7-[4-(4-(6-trifluoromethyl-benzisoxazolyl)-1-piperazinyl)-n-butoxy]-3,4-dihydro-2(1H)-quinolinone hydrochloride 4-trifluoromethyl-salicylic acid is used as a starting material to replace 4-chloro-salicylic acid used in the preparation of compound I-1, to prepare the target compound through the synthesizing process in Example 1.

Element analysis: $C_2H_{27}F_3N_4O_3 \cdot 2HCl$ (calculated value %: C, 53.48; H, 5.21; N, 9.98. found value %: C, 53.26; H, 5.18; N, 9.94).

$^1$HNMR (DMSO-$d_6$): δ9.93 (s, 1H, CONH), 8.04-6.48, (6H, aromatic ring-H), 4.03-4.09 (2H, piperazine-H), 3.98 (t, J=6.4 Hz, 2H, O—CH$_2$,) 3.55-3.60 (2H, piperazine-H), 3.21-3.49 (m, 6H), 2.80 (t, J=8 Hz, 2H), 2.39 (t, J=8 Hz, 2H) 1.80-1.93 (m, 4H)

MS: m/z 488

Example 6

I-6 7-[4-(4-(6-methyl-benzisoxazolyl)-1-piperazinyl)-n-butoxy]-3,4-dihydro-2(1H)-quinolinone hydrochloride 4-methyl-salicylic acid is used as a starting material to replace 4-chloro-salicylic acid used in the preparation of compound I-1, to prepare the target compound through the synthesizing process in Example 1.

Element analysis: $C_{25}H_{30}N_4O_3 \cdot 2HCl$ (calculated value %: C, 59.17; H, 6.36; N, 11.04. found value %: C, 59.05; H, 6.34; N, 11.01).

$^1$HNMR (DMSO-$d_6$): δ9.89 (s, 1H, CONH), 7.94-6.48, (6H, aromatic ring-H), 4.03-4.09 (2H, piperazine-H), 3.87 (t, J=6.4 Hz, 2H, O—CH$_2$,) 3.57-3.60 (2H, piperazine-H), 3.21-3.51 (m, 6H), 2.80 (t, J=8 Hz, 2H), 2.44 (t, J=8 Hz, 2H), 1.79-1.93 (m, 7H)

MS: m/z 434

Example 7

I-7 7-[4-(4-(5-methyl-benzisoxazoly)-1-piperazinyl)-n-butoxy]-3,4-dihydro-2(1H)-quinolinone hydrochloride 5-methyl-salicylic acid is used as a starting material to replace 4-chloro-salicylic acid used in the preparation of compound I-1, to prepare the target compound through the synthesizing process in Example 1.

Element analysis: $C_{25}H_{30}N_4O_3 \cdot 2HCl$ (calculated value %: C, 59.17; H, 6.36; N, 11.04. found value %: C, 58.93; H, 6.32; N, 10.97).

$^1$HNMR (DMSO-$d_6$): δ9.90 (s, 1H, CONH), 7.74-6.48, (6H, aromatic ring-H), 4.09-4.18 (2H, piperazine-H), 3.88 (t, J=6.4 Hz, 2H, O—CH$_2$,) 3.57-3.63 (2H, piperazine-H), 3.20-3.57 (m, 6H), 2.78 (t, J=8 Hz, 2H), 2.43 (t, J=8 Hz, 2H) 1.80-2.01 (m, 7H)

MS: m/z 434

Example 8

I-8 7-[4-(4-(6-hydroxy-benzisoxazolyl)-1-piperazinyl)-n-butoxy]-3,4-dihydro-2(1H)-quinolinone hydrochloride 4-hydroxy-salicylic acid is used as a starting material to replace 4-chloro-salicylic acid used in the preparation of compound I-1, to prepare the target compound through the synthesizing process in Example 1.

Element analysis: $C_{25}H_{28}F_3N_4O_3 \cdot 2HCl$ (calculated value %: C, 53.48; H, 5.21; N, 9.98. found value %; C, 53.26; H, 5.18; N, 9.94).

$^1$HNMR (DMSO-$d_6$): δ9.87 (s, 1H, CONH), 8.04-6.48, (6H, aromatic ring-H), 5.12 (b, 1H, hydroxy-H), 4.10-4.15 (2H, piperazine-H), 3.85 (, J=6.4 Hz, 2H, O—CH$_2$,) 3.60-3.72 (2H, piperazine-H), 3.21-3.53 (m, 6H), 2.84 (t, J=8 Hz, 2H), 2.39 (t, J=8 Hz, 2H) 1.83-2.01 (m, 4H)

MS: m/z 488

Example 9

I-9 7-[4-(4-(5-methoxy-benzisoxazolyl)-1-piperazinyl)-n-butoxy]-3,4-dihydro-2(1H)-quinolinone hydrochloride 5-methoxy-salicylic acid is used as a starting material to replace 4-chloro-salicylic acid used in the preparation of compound I-1, to prepare the target compound through the synthesizing process in Example 1.

Element analysis: $C_{25}H_{30}N_4O_3 \cdot 2HCl$ (calculated value %: C, 57.38; H, 6.16; N, 10.70. found value %: C, 57.13; H, 6.13; N, 10.65).

$^1$HNMR (DMSO-$d_6$): δ9.92 (s, 1H, CONH), 8.04-6.48, (6H, aromatic ring-H), 4.05-4.10 (2H, piperazine-H), 3.80 (b, 5H, O—CH$_2$,) 3.59-3.62 (2H, piperazine-H), 3.20-3.50 (m, 6H), 2.78 (t, J=8 Hz, 2H) 2.41 (t, J=8 Hz, 2H) 1.73-1.93 (m, 4H)

MS: m/z 450

Example 10

I-10 7-[4-(4-(5-cyano-benzisoxazolyl)-1-piperazinyl)-n-butoxy]-3,4-dihydro-2(1H)-quinolinone hydrochloride 5-cyano-salicylic acid is used as a starting material to replace 4-chloro-salicylic acid used in the preparation of compound I-1, to prepare the target compound through the synthesizing process in Example 1.

Element analysis: $C_{25}H_{27}N_5O_3 \cdot 2HCl$ (calculated value %: C, 57.92; H, 5.64; N, 13.51. found value %: C, 57.80; H, 5.62; N, 13.48).

$^1$HNMR (DMSO-$d_6$): δ10.05 (s, 1H, CONH), 7.94-6.48, (6H, aromatic ring-H), 3.95-4.07 (2H, piperazine-H), 3.99 (t, J=6.4 Hz, 2H, O—CH$_2$,) 3.54-3.60 (2H, piperazine-H), 3.11-3.49 (m, 6H), 2.67 (t, J=8 Hz, 2H), 2.39 (t, J=8 Hz, 2H) 1.81-1.98 (m, 4H)

MS: m/z 445

Example 11

I-11 7-[4-(4-(5-bromo-benzisoxazolyl)-1-piperazinyl)-n-butoxy]-3,4-dihydro-2(1H)-quinolinone hydrochloride 5-bromo-salicylic acid is used as a starting material to replace 4-chloro-salicylic acid used in the preparation of compound I-1, to prepare the target compound through the synthesizing process in Example 1.

Element analysis: $C_{24}H_{27}BrN_4O_3 \cdot 2HCl$ (calculated value %: C, 50.37; H, 5.11; N, 9.79. found value %: C, 50.16; H, 5.08; N, 9.75).

$^1$HNMR (DMSO-$d_6$): δ10.01 (s, 1H, CONH), 8.01-6.48 (6H, aromatic ring-H), 4.12-4.23 (2H, piperazine-H), 3.89 (t, J=6.4 Hz, 2H, O—CH$_2$,) 3.50-3.54 (2H, piperazine-H), 3.11-3.51 (m, 6H), 2.80 (t, J=8 Hz, 2H), 2.33 (t, J=8 Hz, 2H) 1.77-1.93 (m, 4H)

MS: m/z 498

Example 12

I-12 7-[4-(4-(7-bromo-6-methoxy-benzisoxazolyl)-1-piperazinyl)-n-butoxy]-3,4-dihydro-2(1H)-quinolinone hydrochloride 3-bromo-salicylic acid is used as a starting material to replace 4-chloro-salicylic acid in the preparation of I-1, to prepare the target compound through the synthesizing process in Example 1.

Element analysis: $C_{25}H_{29}BrN_4O_4 \cdot 2HCl$ (calculated value %: C, 49.85; H, 5.19; N, 9.30. found value %: C, 49.70; H, 6.11; N, 10.61).

$^1$HNMR (DMSO-$d_6$): δ9.93 (s, 1H, CONH), 7.98-6.48, (5H, aromatic ring-H), 4.05-4.10 (2H, piperazine-H), 3.95 (m, J=6.4 Hz, 5H, O—CH$_2$,) 3.59-3.62 (2H, piperazine-H), 3.20-3.50 (m, 6H), 2.78 (t, J=8 Hz, 2H) 2.41 (t, J=8 Hz, 2H) 1.73-1.93 (m, 4H)

MS: m/z 528

Example 13

II-1 7-[4-(4-(6-fluoro-benzisoxazolyl)-1-piperidinyl)-n-butoxy]-3,4-dihydro-2(1H)-quinolinone hydrochloride 1) Preparation of 1-acetyl-4-(2,4-difluorobenzoyl)piperidine 1,3-difluorobenzene (6.7 g, 58.7 mmol) and ammonium chloride (13.3 g, 250 mmol) are added to 15 ml of dichloromethane and cooled to room temperature; thereto is dropadded 50 ml of dichloromethane wherein 1-acetyl-4-piperidinyl carboxylic acid chloride (9.8 g, 51.8 mmol) is dissolved. A reaction is carried out at reflux for 3 hours and the resulting mixture is poured into a mixture of ice and hydrochloric acid after completion of reaction. The mixture is extracted with dichloromethane (20 ml×3). The organic phase is separated, dried over anhydrous magnesium sulfate, filtered, and evaporated to dryness to obtain 5.01 g of a product, with a yield of 36%.

2) Preparation of 2,4-difluorophenyl-(4-piperidinyl)methanone hydrochloride 1-acetyl-4-(2,4-difluorobenzoyl)piperidine (5.6 g, 20.9 mmol) is added to 19 ml of 6N Hydrochloric acid and reflux for 5 hours. The mixture is evaporated to dryness under reduced pressure. The residue is added 20 ml of isopropanol, stirred, filtered, and dried to obtain 4.67 g of a product, with a yield of 85%.

3) Preparation of 2,4-difluorophenyl-(4-piperidinyl)methanone oxime hydrochloride 2,4-difluorophenyl-(4-piperidine)methanone hydrochloride (3.0 g, 11.5 mmol) and hydroxyamine hydrochloride (3.0 g, 42.8 mmol) are added to 5 ml of ethanol; thereto is dropadded 3 ml of N,N-dimethylethanolamine. The mixture is stirred at room temperature, refluxed for 3 hours, and then cooled to room temperature after completion of reaction. The deposit is filtered and dried to obtain 2.6 g of the title compound as a white crystal product, with a yield of 96%.

4) Preparation of 4-(6-fluoro-1,2-benzisoxazolyl)-piperidine 2,4-difluorophenyl-(4-piperidinyl)-methanone oxime hydrochloride (5.52 g, 20 mmol) is added to 25 ml of 50% potassium hydroxide; reflux for 4 hours, cooled to room temperature, and extracted with toluene (25 ml×2). The combined organic phases are dried over anhydrous magnesium sulfate, filtered, evaporated to dryness under reduced pressure, and recrystallized in diethyl ether, to obtain 3.3 g of a product, with a yield of 75%.

5) Preparation of 7-(4-chlorobutoxy)-3,4-dihydro-2(1H)-quinolinone 1-bromo-4-chloro-butane (3.4 g, 20 mmol), anhydrous potassium carbonate powder (4.14 g, 30 mmol) and 7-hydroxy-3,4-dihydro-2(1H)-quinolinone (1.63 g, 10 mmol) are added to 10 ml of acetone and reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder. The powder is slurried with n-hexane (20 ml×3), filtered, and dried to obtain 1.98 g of 7-(4-chlorobutoxy)-3,4-dihydro-2(1H)-quinolinone, with a yield of 78%.

6) Preparation of 7-[4-(4-(6-fluoro-benzisoxazolyl)-1-piperidinyl)-n-butoxy]-3,4-dihydro-2(1H)-quinolinone hydrochloride 7-(4-chlorobutoxy)-3,4-dihydro-2(1H)-quinolinone (297 mg, 1 mmol), 4-(6-fluoro-1,2-benzisoxazolyl)-piperidine (242 mg, 1.1 mmol), and anhydrous potassium carbonate powder (414 mg, 3.3 mmol) are added to 10 ml and react at reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder. The powder is dissolved with 5 ml of acetone and stirred in an ice bath. A white solid precipitates and is filtered, washed with small amount of acetone, and dried to obtain 260 mg of a whiter powder. The powder is dissolved in anhydrous ethanol and then thereto is drop-added HCl/EtOH to adjust to pH=2. A white deposit precipitates and is filtered out and recrystallized in anhydrous ethanol to obtain 200 mg of a product, with a yield of 42%.

Element analysis: $C_{25}H_{28}FN_3O_3$—HCl (calculated value %: C, 63.35; H, 6.17; N, 8.87. found value %: C, 63.22; H, 6.11; N, 8.80).

$^1$HNMR (DMSO-$d_6$): δ9.88 (B, 1H, CONH) 8.00-6.38 (6H, aromatic ring-H) 3.94 (t, J=6.4 Hz, 2H, O—CH$_2$) 3.20 (m, 2H, piperidine-H) 1.51-3.02 (17H, —CH$_2$)

MS: m/z 437

Example 14

II-2 7-[3-(4-(6-fluoro-benzisoxazolyl)-1-piperidinyl)-n-propoxy]-3,4-dihydro-2(1H)-quinolinone hydrochloride 1-bromo-3-chloro-propane is used as a starting material to replace 1-bromo-4-chloro-butane used in the preparation of II-1, to prepare the target compound through the synthesizing process in Example 13.

Element analysis: $C_{24}H_{26}FN_3O_3$.HCl (calculated value %: C, 62.67; H, 5.92; N, 9.14. found value %: C, 62.60; H, 5.95; N, 9.20).

$^1$HNMR (DMSO-$d_6$): δ9.88 (B, 1H, CONH) 7.95-6.52 (6H, aromatic ring-H) 3.91 (t, J=6.4 Hz, 2H, O—CH$_2$) 3.26 (m, 2H, piperidine-H) 1.55-2.83 (15H, —CH$_2$)

MS: m/z 423

Example 15

II-3 7-[5-(4-(6-fluoro-benzisoxazolyl)-1-piperidinyl)-pentyloxy]-3,4-dihydro-2(1H)-quinolinone hydrochloride 1-bromo-3-chloro-propane is used as a starting material to replace 1-bromo-5-chloro-pentane used in the preparation of II-1, to prepare the target compound through the synthesizing process in Example 13.

Element analysis: $C_{26}H_{30}FN_3O_3$.HCl (calculated value %: C, 63.99; H, 6.40; N, 8.61. found value %: C, 63.90; H, 8.44; N, 8.60).

$^1$HNMR (DMSO-$d_6$): δ10.02 (B, 1H, CONH) 8.12-6.56, (6H, aromatic ring-H) 3.81 (t, J=6.4 Hz, 2H, O—CH$_2$) 3.20 (m, 2H, piperidine-H) 1.46-2.91 (19H, —CH$_2$)

MS (APCI): m/z 451[M+H]$^+$

Example 16

II-4 7-[(4-benzisoxazolyl-1-piperidinyl)-n-butoxy]-3,4-dihydro-2(1H)-quinolinone hydrochloride 1) Preparation of 4-(2-fluoro-phenyl)-1-methylpiperidine 800 ml of THF solution of 4-chloro-N-methylpiperidine (245 g, 1.8 mol) is drop-added slowly to 250 ml of tetrahydrofuran wherein Mg powder (55.7 g, 2.3 mol) and small amount of ethyl bromide are added under coverage of N$_2$. After completion of drop-addition, a reaction is carried out at reflux for one hour. The reaction solution is drop-added 440 ml of THF solution of 2-fluorobenzonitrile (222 g, 1.8 mol). After completion of drop-addition, a reaction is carried out at reflux for 3 hours and at room temperature for 13 hours; thereafter the reaction solution is poured into 2.3 L of water containing 700 g of NH$_4$Cl and then reflux for 2 hours. The reaction solution is cooled and then is extracted with diethyl ether, and the extracting solutions are combined, evaporated to dryness and fractioned. The fractions at 124° C. are collected to obtain 224 g of a product.

2) Preparation of 3-(1-methyl-4-piperidinyl)-1,2-benzisothiazole hydrochloride

To a ethyl glycol (400 ml)-water (200 ml) solution of 4-(2-fluoro-phenyl)-1-methylpiperidine hydrochloride (28.2 g, 0.13 mmol) and hydroxyamine hydrochloride (19.2 g, 0.28 mol) is added 200 ml of 85% KOH (80.8 g, 1.2 mol) aqueous solution, and a reaction is carried out under reflux for 5 hours under coverage of N$_2$. After completion of reaction, the reaction solution is poured into 1000 ml of water and extracted with diethyl ether. The extracting solutions are combined, dried, dissolved with small amount of acetone, and adjusted with HCl/EtOH to pH=2. A large amount of white deposit precipitates and is recrystallized in EtOH—H$_2$O to obtain 15.4 g of a product.

3) Preparation of 3-(4-piperidinyl)-1,2-benzisothiazole hydrochloride

To a toluene solution of 3-(1-methyl-4-piperidinyl)-1,2-benzisothiazole (12.3 g) is added phenoxy formyl chlorine (8.8 g, 0.056 mol) and react for 16 hours under coverage of N$_2$. The reaction is cooled and filtered. The filtrate is concentrated to obtain a product as an oil, which is dissolved into diethyl ether and thereto is drop-added petroleum ether to precipitate a white solid. 5 g of the white solid is dissolved into 5 g of KOH solution and reflux for 16 hours. Ethanol is removed by evaporation to obtain a product as a brown oil. The oil is dissolved into small amount of acetone and thereto is drop-added HCl/EtOH to adjust to pH=2. Thereafter a white solid precipitates and is recrystallized in methanol-water to obtain 2.0 g of a product.

4) Preparation of 7-[4-(4-benzisoxazolyl-1-piperidinyl)-butoxy]-3,4-dihydro-2(1H)-quinolinone hydrochloride 7-(4-chlorobutoxy)-3,4-dihydro-2(1H)-quinolinone (297 mg, 1 mmol), 3-(4-piperidinyl)-1,2-benzisothiazole (220 mg, 1 mmol), and anhydrous potassium carbonate powder (414 mg, 3.3 mmol) are added to 10 ml and react at reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder, which is dissolved into 5 ml of acetone and stirred in an ice bath to precipitate a white solid. The white solid is filtered, washed with small amount of acetone, and dried to obtain 260 mg of a whiter powder. The whiter powder is dissolved into anhydrous ethanol and thereto is drop-added HCl/EtOH to adjust to pH=2 to precipitate a white deposit, which is filtered out and recrystallized in anhydrous ethanol to obtain 200 mg of a product, with a yield of 44%.

Element analysis: $C_{25}H_{29}N_3O_3 \cdot HCl$ (calculated value %: C, 65.85; H, 6.63; N, 9.22. found value %; C, 65.82; H, 6.60; N, 9.25).

$^1$HNMR (DMSO-$d_6$): δ9.88 (B, 1H, CONH) 7.91-6.38 (6H, aromatic ring-H) 3.87 (t, J=6.4 Hz, 2H, O—CH$_2$) 3.22 (m, 2H, piperidine-H) 1.58-2.99 (18H, —CH$_2$)

MS: m/z 419

Example 17

II-5 7-[4-(4-(6-chloro-benzisoxazolyl)-1-piperidinyl)-n-butoxy]-3,4-dihydro-2(1H)-quinolinone hydrochloride 1-chloro-3-fluorobenzene is used as starting material to replace 1,3-difluorobenzene used in the preparation of II-1, to prepare the target compound through the synthesizing process in Example 13.

Element analysis: $C_{23}H_{28}ClN_{33}O_3 \cdot HCl$ (calculated value %: C, 61.23; H, 5.96; N, 8.57. found value %: C, 61.20; H, 5.93; N, 8.60).

$^1$HNMR (DMSO-$d_6$): δ9.88 (8, 1H, CONH) 8.08-6.40 (6H, aromatic ring-H) 3.89 (t, J=6.4 Hz, 2H, O—CH$_2$) 3.14 (m, 2H, piperidine-H) 1.40-2.95 (17H, —CH$_2$)

MS: m/z 453

Example 18

II-6 7-[4-(4-(5-methoxy-benzisoxazolyl)-1-piperidinyl)-n-butoxy]-3,4-dihydro-2(1H)-quinolinone hydrochloride

1) Preparation of (4-(2-hydroxy-5-methoxyphenyl)(1-acetyl-piperidinyl)methanone oxime hydrochloride 4-methoxyphenol is used as a starting material, to prepare (4-(2-hydroxy-5-methoxyphenyl)(1-acetyl-piperidinyl)methanone oxime hydrochloride according to steps 1, 2 and 3 in synthesizing of II-1.

2) Preparation of 1-acetyl-4-(5-methoxy-1,2-benzisoxazolyl)piperidine 0.034 mol of free (4-(2-hydroxy-5-methoxyphenyl)(1-acetyl-piperidinyl)methanone oxime is reacted with 4.5 ml of acetic anhydride at 60° C. for 1.5 hours, and then the acetic anhydride is removed by evaporation to obtain an acylated product. The product is added to 80 ml of DMF wherein NaH (1.1 g, 0.023 mol) is suspended. A reaction is carried out at room temperature for 16 hours and the reaction solution is poured into 300 ml of water and extracted with ethyl acetate. The organic phase is washed with water and saturated saline successively, and dried over anhydrous mgSO$_4$ to obtain a product as an oil, which is crystallized in diethyl ether to obtain 3.7 g of a solid, which is recrystallized in toluene-cyclohexane to obtain 2.1 g of 1-acetyl-4-(5-methoxy-1,2-benzisoxazolyl)piperidine.

3) Preparation of 4-(5-methoxy-1,2-benzisoxazolyl)piperidine hydrochloride 0.07 mol of 1-acetyl-4-(5-methoxy-1,2-benzisoxazolyl)piperidine and 110 ml of 6N HCl is refluxed for 6 hours and stand at room temperature to precipitate large amount of white deposit, which is recrystallized in ethanol to obtain 4-(5-methoxy-1,2-benzisoxazolyl)piperidine hydrochloride.

4) Preparation of 7-[4-(4-(5-methoxy-benzisoxazolyl)-1-piperidinyl)-n-butoxy]-3,4-dihydro-2(1H)-quinolinone hydrochloride Preparing 7-[4-(4-(5-methoxy-benzisoxazoly)-1-piperidinyl)-n-butoxy]-3,4-dihydro-2(1H)-quinolinone hydrochloride according to step 4 in Example 13, with a yield of 52%.

Element analysis: $C_{26}H_{31}N_3O_4$—HCl (calculated value %: C, 64.25; H, 6.64; N, 8.15. found value %: C, 64.22; H, 6.51; N, 8.19).

$^1$HNMR (DMSO-$d_6$): δ9.88 (B, 1H, CONH) 7.95-6.38 (6H, aromatic ring-H) 3.92 (t, J=6.4 Hz, 2H, O—CH$_2$) 3.18 (m, 2H, piperidine-H) 1.54-3.02 (20H, —CH$_2$)

MS: m/z 449

Example 19

II-7 7-[4-(4-(5-fluoro-benzisoxazolyl)-1-piperidinyl)-n-butoxy]-3,4-dihydro-2(1H)-quinolinone hydrochloride 4-fluorophenol is used as a starting material to replace 1,3-difluorobenzene used in the preparation of II-1, to prepare the target compound through the synthesizing process in Example 13.

Element analysis: $C_{25}H_{28}FN_3O_3 \cdot HCl$ (calculated value %: C, 63.35; H, 6.17; N, 8.87. found value %: C, 63.31; H, 6.15; N, 8.85).

$^1$HNMR (DMSO-$d_6$): δ9.88 (B, 1H, CONH) 7.96-6.38 (6H, aromatic ring-H) 3.95 (t, J=6.4 Hz, 2H, O—CH$_2$) 3.27 (m, 2H, piperidine-H) 1.56-2.83 (18H, —CH$_2$)

MS: m/z 437

Example 20

II-8 7-[4-(4-(5,6-dimethoxy-benzisoxazolyl)-1-piperidinyl)-n-butoxy]-3,4-dihydro-2(1H)-quinolinone hydrochloride 3,4-dimethoxyphenol is used as a starting material to replace 1,3-difluorobenzene used in the preparation of II-1, to prepare the target compound through the synthesizing process in Example 13.

Element analysis: $C_{27}H_3N_3O_5 \cdot HCl$ (calculated value %: C, 62.84; H, 6.64; N, 8.14. found value %: C, 62.82; H, 6.62; N, 8.16).

$^1$HNMR (DMSO-$d_6$): δ9.88 (B, 1H, CONH) 8.08-6.40 (5H, aromatic ring-H) 3.89-3.35 (m, 8H, O—$CH_2$) 3.20 (m, 2H, piperidine-H) 1.53-2.97 (17H, —$CH_2$)

MS: m/z 479

Example 21

II-9 7-[4-(5-hydroxy-benzisoxazolyl)-1-piperidinyl)-n-butoxy]-3,4-dihydro-2(1H)-quinolinone hydrochloride 2.1 g of 1-acetyl-4-(5-methoxy-1,2-benzisoxazolyl)piperidine obtained in Example 18 and 25 ml of 48% HBr solution react at reflux for 4 hours, and at room temperature for 10 hours successively to precipitate a white deposit, which is filtered out and recrystallized in methanol-diethyl ether to obtain 1.0 g of 5-hydroxy-3-(4-piperidinyl)-1,2-benzisoxazole hydrobromide, and preparing 7-[4-(4-(5-hydroxy-benzisoxazolyl)-1-piperidinyl)-n-butoxy]-3,4-dihydro-2(1H)-quinolinone hydrochloride according to step 4 in Example 13, with a yield of 49.3%.

Element analysis: $C_{25}H_{29}N_3O_4 \cdot HCl$ (calculated value %: C, 63.62; H, 6.41; N, 8.90. found value %: C, 63.58; H, 6.30; N, 8.97).

$^1$HNMR (DMSO-$d_6$): δ9.88 (B, 1H, CONH) 8.08-6.40 (6H, aromatic ring-H) 5.13 (b, 1H, hydroxy-H) 3.89 (t, J=6.4 Hz, 2H, O—$CH_2$) 3.14 (m, 2H, piperidine-H) 1.40-2.95 (17H, —$CH_2$)

MS: m/z 435

Example 22

II-10 7-[4-(5,6-dihydroxy-benzisoxazolyl)-1-piperidinyl)-n-butoxy]-3,4-dihydro-2(1H)-quinolinone hydrochloride 2.1 g of 1-acetyl-4-(5,6-dimethoxy-1,2-benzisoxazolyl)piperidine obtained in Example 20 and 25 ml of 48% HBr solution react at reflux for 4 hours, and at room temperature for 10 hours to precipitate a white deposit. The deposit is filtered out and recrystallized in methanol-diethyl ether to obtain 1.0 g of 5-hydroxy-3-(4-piperidinyl)-1,2-benzisoxazole hydrobromide, which is used according to step 4 in Example 13 to obtain 7-[4-(4-(5,6-dihydroxy-benzisoxazolyl)-1-piperidinyl)-n-butoxy]-3,4-dihydro-2(1H)-quinolinone hydrochloride, with a yield of 61%.

Element analysis: $C_{25}H_{29}N_3O_5 \cdot HCl$ (calculated value %: C, 61.53; H, 6.20; N, 8.61. found value %: C, 61.43; H, 6.30; N, 8.71).

$^1$HNMR (DMSO-$d_6$): δ9.88 (B, 1H, CONH) 8.08-6.40 (5H, aromatic ring-H) 5.20 (b, 2H, hydroxy-H) 3.80 (t, J=6.4 Hz, 2H, O—$CH_2$) 3.21 (m, 2H, piperidine-H) 1.50-2.93 (17H, —$CH_2$)

MS: m/z 451

Example 23

II-11 Preparation of (E)-7-[4-(4-(3-(6-fluoro-benzisoxazolyl))-1-piperidinyl)-2-butenyloxy]-3,4-dihydro-2(1H)-quinolinone (E)-1,4-dichloro-2-butene and 4-(3-(6-fluoro-benzisoxazolyl))-1-piperidine are used as starting materials and react according to the method of preparation of II in Method 1 to prepare (E)-3-(1-4-(4-chloro-2-butenyl)piperidinyl))-6-fluorobenzisoxazole.

(E)-3-(1-4-(4-chloro-2-butenyl)piperidinyl))-6-fluorobenzisoxazole and 7-hydroxy-3,4-dihydro-2(1H)-quinolinone are used as starting materials and react according to step 4 in the following method of preparation of IV-1 to obtain E-7-[4-(4-(3-(6-fluoro-benzisoxazolyl))-1-piperidinyl)-2-butenyloxy]-3,4-dihydro-2(1H)-quinolinone, with a yield of 52%.

Element analysis: $C_{25}H_{26}FN_3O_3$ (calculated value %: C, 68.95; H, 6.02; N, 9.65. found value %: C, 68.99; H, 6.07; N, 9.61).

$^1$HNMR (DMSO-$d_6$): δ9.89 (B, 1H, CONH) 8.08-6.40 (5H, aromatic ring-H) 5.20 (b, 2H, hydroxy-H) 3.80 (t, J=6.4 Hz, 2H, O—$CH_2$) 3.21 (m, 2H, piperidine-H) 1.50-2.93 (17H, —$CH_2$)

MS: m/z 435

Example 24

II-12 Preparation of (Z)-7-[4-(4-(3-(6-fluoro-benzisoxazolyl))-1-piperidinyl)-2-butenyloxy]-3,4-dihydro-2(1H)-quinolinone 1,4-dichloro-2-butene and 4-(3-(6-fluoro-benzisoxazolyl))-1-piperidine are used as starting materials and react according to the method of preparation of II in Method 1 to obtain (E)-3-(1-4-(4-chloro-2-butenyl)piperidinyl))-6-fluorobenzisoxazole.

(E)-3-(1-4-(4-chloro-2-butenyl)piperidinyl))-6-fluorobenzisoxazole and 7-hydroxy-3,4-dihydro-2(1H)-quinolinone are used as starting materials and react according to step 4 in the following method of preparation of IV-1 to obtain E-7-[4-(4-(3-(6-fluoro-benzisoxazolyl))-1-piperidinyl)-2-butenyloxy]-3,4-dihydro-2(1H)-quinolinone, with a yield of 55%.

Element analysis: $C_{25}H_{26}FN_3O_3$ (calculated value %: C, 68.95; H, 6.02; N, 9.65. found value %: C, 68.99; H, 6.07; N, 9.61).

$^1$HNMR (DMSO-$d_6$): δ9.91 (B, 1H, CONH) 8.08-6.40 (5H, aromatic ring-H) 5.20 (b, 2H, hydroxy-H) 3.80 (t, J=6.4 Hz, 2H, O—$CH_2$) 3.21 (m, 2H, piperidine-H) 1.50-2.93 (17H, —$CH_2$)

MS: m/z 435

Example 25

II-13

7-(((1R,2S)-2-(4-(3-(6-fluoro-benzisoxazolyl))-1-piperidinyl)methyl)cyclohexyl)methoxy)-3,4-dihydro-2(1H)-quinolinone 1) 1,2-dichloromethylcyclohexane and 4-(3-(6-fluoro-benzisoxazolyl))-1-piperidine are used as starting materials and react according to the method of preparation of III in Method 1 to obtain 3-(4-(1-(((1R,2S)-2-(chloromethyl)cyclohexyl)methylpiperidinyl))-6-fluoro-benzisoxazole.

2) 3-(4-(1-(((1R,2S)-2-(chloromethyl)cyclohexyl)methylpiperidinyl))-6-fluoro-benzisoxazole and 7-hydroxy-3,4-dihydro-2(1H)-quinolinone are used as starting materials and react according to step 4 in the following method of preparation of IV-1 to obtain 7-(((1R,2S)-2-(4-(3-(6-fluoro-benzisoxazolyl))-1-piperidinyl)methyl)cyclohexyl)methoxy)-3,4-dihydro-2(1H)-quinolinone, with a yield of 65%.

Element analysis: $C_{29}H_{34}FN_3O_3$ (calculated value %: C, 70.85; H, 6.97; N, 8.55. found value %: C, 70.81; H, 6.90; N, 8.61).

$^1$HNMR (DMSO-$d_6$): δ9.889 (B, 1H, CONH) 8.08-6.40 (5H, aromatic ring-H) 5.20 (b, 2H, hydroxy-H) 3.80 (t, J=6.4 Hz, 2H, O—$CH_2$) 3.21 (m, 2H, piperidine-H) 1.50-2.93 (17H, —$CH_2$)

MS: m/z 491

Example 26

II-14

7-(((1R,2R)-2-(4-(3-(6-fluoro-benzisoxazolyl))-1-piperidinyl)methyl)cyclohexyl)methoxy)-3,4-dihydro-2(1H)-quinolinone 1) (1R,2R)-1,2-dichloromethylcyclohexane and 4-(3-(6-fluoro-benzisoxazolyl))-1-piperidine are used as starting materials and react to according to the method of preparation of III in Method 1 to obtain 3-(4-(1-(((1R,2R)-2-(chloromethyl)cyclohexyl)methylpiperidinyl))-6-fluoro-benzisoxazole.

2) 3-(4-(1-(((1R,2R)-2-(chloromethyl)cyclohexyl)methylpiperidinyl))-6-fluoro-benzisoxazole and 7-hydroxy-3,4-dihydro-2(1H)-quinolinone are used as starting materials and react according to step 4 in the following method of preparation of IV-1 to obtain 7-(((1R,2R)-2-(4-(3-(6-fluoro-benzisoxazolyl))-1-piperidinyl)methyl)cyclohexyl)methoxy)-3,4-dihydro-2(1H)-quinolinone, with a yield of 65%.

Element analysis: $C_{29}H_{34}FN_3O_3$ (calculated value %: C, 70.85; H, 6.97; N, 8.55. found value %: C, 70.81; H, 6.90; N, 8.61).

$^1$HNMR (DMSO-$d_6$): δ9.889 (B, 1H, CONH) 8.08-6.40 (5H, aromatic ring-H) 5.20 (b, 2H, hydroxy-H) 3.80 (t, J=6.4 Hz, 2H, O—$CH_2$) 3.21 (m, 2H, piperidine-H) 1.50-2.93 (17H, —$CH_2$)

MS: m/z 491

Example 27

III-1 7-[4-(1,2-benzisothiazol-3-yl)-1-piperazinyl)-n-butoxy]-3,4-dihydro-2(1H)-quinolinone hydrochloride

1) Preparation of 7-(4-chlorobutoxy)-3,4-dihydro-2(1H)-quinolinone 1-bromo-4-chloro-butane (3.4 g, 20 mmol), anhydrous potassium carbonate powder (4.14 g, 30 mmol) and 7-hydroxy-3,4-dihydro-2(1H)-quinolinone (1.63 g, 10 mmol) are added to 10 ml of acetone and reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder. The powder is slurried in n-hexane (20 ml×3), filtered, and dried to obtain 1.98 g of 7-(4-chlorobutoxy)-3,4-dihydro-2(1H)-quinolinone, with a yield of 78%.

2) Preparation of 4-(1,2-benzisothiazol-3-yl)-1-piperazine 3-chloro-(1,2-benzisothiazole) (14 g, 200 mmol) and anhydrous piperazine (6.8 g, 40 mmol) are placed in an egg type flask and heated at 125° C. for 24 hours. After completion of reaction, 52 ml of an ice-water mixture is added for quenching the reaction. The mixture is further added with 3.2 g of 50% NaOH solution, stirred 5 minutes and extracted with $CH_2Cl_2$ (50 ml×3). The organic layer is washed with an ice-water mixture (50 ml×2) and saturated saline (50 ml×2), and dried over anhydrous $MgSO_4$ to obtain 4-(1,2-benzisothiazol-3-yl)-1-piperazine.

3) Preparation of 7-[4-(1,2-benzisothiazol-3-yl)-1-piperazinyl)-n-butoxy]-3,4-dihydro-2(1H)-quinolinone hydrochloride 7-(4-chlorobutoxy)-3,4-dihydro-2(1H)-quinolinone (297 mg, 1 mmol), 4-(1,2-benzisothiazol-3-yl)-1-piperidine (242 mg, 1.1 mmol), and anhydrous potassium carbonate powder (414 mg, 3.3 mmol) are added to 10 ml and react at reflux for 24 hours. The reaction solution is evaporated to dryness and dispersed with 20 ml of dichloromethane and 20 ml of water respectively. The organic layer is extracted with water (20 ml×2) and saturated saline (20 ml) successively, dried over anhydrous magnesium sulfate, and evaporated to dryness to obtain a light yellow powder. The powder is dissolved with 5 ml of acetone and stirred in an ice bath to precipitate a white solid. The solid is filtered, dissolved in small amount of ethanol and adjusted with HCl/EtOH to pH=2 to precipitate a white deposit. The deposit is filtered out to obtain 260 mg of a product, with a yield of 59%.

Element analysis: $C_{24}H_{28}N_4O_2S·2HCl$ (calculated value %: C, 686.03; H, 6.46; N, 12.80. found value %: C, 66.10; H, 6.40; N, 12.70).

$^1$HNMR (DMSO-$d_6$): δ9.98 (s, 1H, CONH), 8.13-6.45, (7H, aromatic ring-H), 4.05-4.10 (2H, piperazine-H), 3.95 (t, J=6.4 Hz, 2H, O—$CH_2$,) 3.59-3.62 (2H, piperazine-H), 3.20-3.50 (m, 6H), 2.78 (t, J=8 Hz, 2H) 2.41 (t, J=8 Hz, 2H) 1.73-1.93 (m, 4H)

MS: 437 [M+H]

Example 28

III-2 7-[3-(1,2-benzisothiazolyl)-1-piperazinyl]-n-propoxy]-3,4-dihydro-2(1H)-quinolinone hydrochloride 1-bromo-3-chloro-propane is used as a starting material to prepare the target product according to the procedure in Method 1.

Element analysis: $C_{23}H_{28}N_4O_2S·2HCl$ (calculated value %: C, 55.75; H, 5.70; N, 11.31. found value %: C, 55.69; H, 5.81; N, 11.30).

$^1$HNMR (DMSO-$d_6$): δ10.02 (s, 1H, CONH), 8.05-6.50, (7H, aromatic ring-H), 4.07-4.12 (2H, piperazine-H), 3.95 (t, J=6.4 Hz, 2H, O—$CH_2$,) 3.62-3.66 (2H, piperidine-H), 3.15-3.47 (m, 8H), 2.80 (t, J=8 Hz, 2H), 2.47 (t, J=8 Hz, 2H) 1.89-2.15 (m, 2H)

MS: m/z 423 [M+H]$^+$

Example 29

III-3 7-[2-(1,2-benzisothiazolyl)-1-piperazinyl]-ethoxy]-3,4-dihydro-2(1H)-quinolinone of 1-bromo-2-chloro-ethane is used as a starting material to prepare the target product according to the procedure in Method 1.

Element analysis: $C_{22}H_{24}N_4O_2S·2HCl$ (calculated value %: C, 54.88; H, 5.44; N, 11.64. found value %: C, 54.87; H, 5.40; N, 11.60).

$^1$HNMR (DMSO-d$_6$): δ10.02 (s, 1H, CONH), 8.01-6.50, (7H, aromatic ring-H), 4.12-4.18 (2H, piperazine-H), 3.99 (t, J=6.4 Hz, 2H, O—CH$_2$,) 3.69-3.78 (2H, piperidine-H), 3.25-3.57 (m, 6H), 2.74 (t, J=8 Hz, 2H), 2.68 (t, J=8 Hz, 2H)
MS: m/z 409 [M+H]$^+$ Example 30

III-4 7-[4-(6-methoxy-1,2-benzisothiazolyl)-1-piperazinyl]-n-butoxy]-3,4-dihydro-2(1H)-quinolinone of hydrochloride 1) Preparation of 6-methoxy-(1,2-benzisothiazolyl)-1-piperazine The title compound is prepared according to the method in J. Med. Chem. 1991, 34, 3316-3328, with a yield of 20%.

2) 7-[4-(6-methoxy-1,2-benzisothiazolyl)-1-piperazinyl)-n-butoxy]-3,4-dihydro-2(1H)-quinolinone hydrochloride 7-[4-(6-methoxy-1,2-benzisothiazolyl)-1-piperazinyl]-n-butoxy)-3,4-dihydro-2(1H)-quinolinone hydrochloride is prepared according to step 7 in Example 1, with a yield of 40%.
Element analysis: C$_{25}$H$_{30}$N$_4$O$_3$S.2HCl (calculated value %: C, 55.65; H, 5.98; N, 10.38. found value %: C, 55.60; H, 5.95; N, 10.30).
$^1$HNMR (DMSO-d$_6$): δ10.01 (s, 1H, CONH), 8.21-6.56, (6H, aromatic ring-H), 4.08-4.15 (2H, piperazine-H), 3.79 (m, 5H, O—CH$_2$,) 3.52-3.60 (2H, piperazine-H), 3.16-3.48 (m, 6H), 2.79 (t, J=8 Hz, 2H), 2.47 (t, J=8 Hz, 2H) 1.82-2.01 (m, 4H)
MS: m/z 466

Example 31

III-5 7-[4-(7-methoxy-1,2-benzisothiazolyl)-1-piperazinyl]-n-butoxy-3,4-dihydro-2(1H)-quinolinone hydrochloride 1) Preparation of 7-methoxy-(1,2-benzisothiazole)-1-piperazine The title compound is prepared according to the method in J. Med. Chem. 1991, 34, 3316-3328, with a yield of 35%.

2) 7-[4-(7-methoxy-1,2-benzisothiazolyl)-1-piperazinyl)-n-butoxy]-3,4-dihydro-2(1H)-quinolinone hydrochloride 7-[4-(7-methoxy-1,2-benzisothiazolyl)-1-piperazinyl]-n-butoxy]-3,4-dihydro-2(1H)-quinolinone hydrochloride is prepared according to step 7 in Example 1, with a yield of 40%.
Element analysis: C$_{25}$H$_{30}$N$_4$O$_3$S.2HCl (calculated value %: C, 55.65; H, 5.98; N, 10.38. found value %: C, 55.62; H, 5.75; N, 10.37).
$^1$HNMR (DMSO-d): δ10.05 (s, 1H, CONH), 8.16-6.50, (6H, aromatic ring-H), 4.10-4.18 (2H, piperazine-H), 3.89 (m, 5H, O—CH$_2$) 3.51-3.60 (2H, piperazine-H), 3.22-3.48 (m, 6H), 2.76 (t, J=8 Hz, 2H), 2.44 (t, J=8 Hz, 2H) 1.72-1.96 (m, 4H)
MS: m/z 468

Example 32

III-6 7-[4-(5-methoxy-1,2-benzisothiazolyl)-1-piperazinyl]-n-butoxy]-3,4-dihydro-2(1H)-quinolinone hydrochloride 1) Preparation of 5-methoxy-(1,2-benzisothiazolyl)-1-piperazine The title compound is prepared according to the method in J. Med. Chem. 1991, 34, 3316-3328, with a yield of 36%, 2) 7-[4-(5-methoxy-1,2-benzisothiazolyl)-1-piperazinyl)-n-butoxy)-3,4-dihydro-2(1H)-quinolinone hydrochloride 7-[4-(5-methoxy-1,2-benzisothiazolyl)-1-piperazinyl]-n-butoxy]-3,4-dihydro-2(1H)-quinolinone hydrochloride is prepared according to step 7 in Example 1, with a yield of 39%.
Element analysis: C$_{25}$H$_{30}$N$_4$O$_3$S.2HCl (calculated value %: C, 55.65; H, 5.98; N, 10.38. found value %: C, 55.62; H, 5.75; N, 10.37).
$^1$HNMR (DMSO-d$_6$): δ10.00 (s, 1H, CONH), 8.17-6.39 (6H, aromatic ring-H), 4.12-4.18 (2H, piperazine-H), 3.91 (m, 5H, O—CH$_2$,) 3.54-3.60 (2H, piperazine-H), 3.18-3.47 (m, 6H), 2.69 (t, J=8 Hz, 2H), 2.45 (t, J=8 Hz, 2H) 1.79-1.98 (m, 4H)
MS: m/z 466

Example 33

III-7 7-[4-(4-methoxy-1,2-benzisothiazolyl)-1-piperazinyl]-n-butoxy]-3,4-dihydro-2(1H)-quinolinone hydrochloride 1) Preparation of 4-methoxy-(1,2-benzisothiazolyl)-1-piperazine The title compound is prepared according to the method in J. Med. Chem. 1991, 34, 3316-3328, with a yield of 41%.

2) Preparation of 7-[4-(4-methoxy-1,2-benzisothiazolyl)-1-piperazinyl]-n-butoxy-3,4-dihydro-2(1H)-quinolinone hydrochloride 7-[4-(4-methoxy-1,2-benzisothiazolyl)-1-piperazinyl]-n-butoxy]-3,4-dihydro-2(1H)-quinolinone hydrochloride is prepared according to step 7 in Example 1, with a yield of 39%.
Element analysis: C$_{25}$H$_{30}$N$_4$O$_3$S.2HCl (calculated value %: C, 55.65; H, 5.98; N, 10.38. found value %: C, 55.63; H, 5.71; N, 10.36).
$^1$HNMR (DMSO-d$_6$): δ10.02 (s, 1H, CONH), 8.14-6.49, (6H, aromatic ring-H), 4.10-4.16 (2H, piperazine-H), 3.87 (m, 5H, O—CH$_2$,) 3.60-3.68 (2H, piperazine-H), 3.19-3.54 (m, 6H), 2.75 (t, J=8 Hz, 2H), 2.42 (t, J=8 Hz, 2H) 1.71-1.80 (m, 4H)
MS: m/z 466

Example 34

IV-1 6-[4-(4-(3-(6-fluoro-benzisoxazolyl))-1-piperidinyl]-n-butoxy)-indoline-2-one 1) 2 ml of pyridine is added to 30 ml of a solution of 3-methoxyaniline (4.92 g, 40 mmol) in dichloromethane and the mixture is stirred for 5 minutes, while maintaining the temperature inside vessel at lower than 0° C., and thereto 20 ml of a solution of chloroacetyl chloride (6.78 g, 60 mmol) in dichloromethane is drop-added slowly. A reaction is carried out at room temperature for 12 hours after completion of drop-addition, and then terminated. The reaction solution is washed with 5% of HCl (30 ml×3), 5% of NaOH (30 ml×3), water (30 ml×3), and saturated saline (30 ml) successively, dried over anhydrous magnesium sulfate and filtered. The filtrate is evaporated to remove the solvent to obtain 6.43 g of 2-chloro-N-(3-methoxyphenyl)acetamide, with a yield of 80.7%.

2) 2-chloro-N-(3-methoxyphenyl)acetamide (3.1 g, 16 mmol) and anhydrous $AlCl_3$ powder (4.4 g, 32 mmol) is heated and stirred at 120° C. for 10 minutes and exhibit a melting state. The temperature is elevated gradually to 240° C. in 40 minutes and then stirred 5 minutes. The reaction is allowed to cool to obtain a brown powder. The solid powder is poured into a mixture of 100 g of crushed ice and 50 ml of concentrated hydrochloric acid. The mixture is stirred for 10 minutes and then reflux for 10 minutes, and allowed to cool to precipitate a light yellow powder, which is filtered out and recrystallized in water to obtain 1.5 g of 6-hydroxy-indoline-2-one, with a yield of 62%.

3) 1-bromo-4-chlorobutane (9.4 g, 60 mmol) is dissolved in 50 ml of DMF, and thereto 4-(6-fluoro-1,2-benzisoxazolyl)-piperidine (4.4 g, 20 mmol) and anhydrous potassium carbonate powder (8.2 g, 60 mmol) is added. The mixture is stirred at room temperature for 48 hours and the reaction is terminated. To the reaction solution is added 100 ml of water and 100 ml of ethyl acetate. The mixture is shaked and the aqueous layer is further extracted with 100 ml of ethyl acetate. The ethyl acetate layers are combined, backwashed with 200 ml of water, dried over anhydrous magnesium sulfate and filtered. The filtrate is concentrated to 50 ml volume and extracted with 5% HCl (30 ml×3). The extracting solution is combined, adjusted to pH 7 with 5% NaOH, and further extracted with ethyl acetate (30 ml×3). The extracting solution is combined, dried and evaporated to dryness to obtain 1.8 g of 3-(1-(4-chlorobutyl)-4-piperidinyl)-6-fluoro-benzisoxazole, with a yield of 30%.

4) 6-hydroxy-indoline-2-one (0.75 g, 5 mmol), 3-(1-(4-chlorobutyl)-4-piperidinyl)-6-fluoro-benzisoxazole (1.55 g, 5 mmol) and anhydrous potassium carbonate (1.38 g, 10 mmol) are added to 10 ml of DMF and react at 60° C. for 12 hours. The reaction solution is added with 20 ml of water and stirred for 30 minutes, and then is added with 2 ml of anhydrous ethanol, subjected to a sonication for 5 minutes and filtered to obtain 500 mg of 6-[4-(4-(3-(6-fluoro-benzisoxazolyl))-1-piperidinyl)-n-butoxy)-indoline-2-one, with a yield of 32%.

Element analysis: $C_{24}H_{26}FN_3O_3$ (calculated value %: C, 69.07; H, 6.28; N, 9.92. found value %: C, 69.12; H, 6.38; N, 9.95).

$^1$HNMR (DMSO-$d_6$): δ10.08 (s, 1H, CONH), 8.23-6.65, (6H, aromatic ring-H), 4.34-4.12 (2H, piperazine-H), 3.76 (m, 5H, O—$CH_2$,) 3.45-3.78 (2H, piperazine-H), 3.21-3.77 (m, 6H), 3.10 (t, J=8 Hz, 2H), 2.30 (t, J=8 Hz, 2H) 1.71-1.90 (m, 4H)

MS: m/z 423

Example 35

IV-2 5-[4-(4-(3-(6-fluoro-benzisoxazolyl))-1-piperidinyl)-n-butoxy)-2(3H)-benzoxazolone 1) To a solution of benzoxazolone (2.0 g, 7.4 mmol) in trifluoroacetic acid (30 ml) is added 30 ml of a solution of trifluoroacetyloxyiodobenzene (7.64 g, 8.9 mmol) in trifluoroacetic acid. The mixture react at reflux for 3 minutes after completion of addition. The reaction is terminated and evaporated to remove most of the trifluoroacetic acid. The residue is drop-added with 5% of $NaHCO_3$ aqueous solution in an ice bath to be adjusted to pH=8 and extracted with ethyl acetate (20 ml×3). The ethyl acetate layers are combined, washed with 50 ml of saturated saline, dried over anhydrous magnesium sulfate and filtered. The filtrate is evaporated to obtain a product as an oil. The oil is then subjected to a separation on a column of neutral alumina (200-300 mesh) eluting at $CH_2Cl_2$:MeOH-200:1 to $CH_2Cl_2$:MeOH-100:1. The elution is combined and evaporated to dryness to obtain 500 mg of 6-hydroxybenzisoxazole, with a yield of 45%.

2) 6-hydroxybenzisoxazole and 3-(1-(4-chlorobutyl)-4-piperidinyl)-6-fluoro-benzisoxazole are used as starting materials and react according to step 4 in the method of preparation of IV-1 to obtain 5-[4-(4-(3-(6-fluoro-benzisoxazolyl))-1-piperidinyl)-n-butoxy)-2(3H)-benzoxazolone, with a yield of 56%.

Element analysis: $C_{23}H_{24}FN_3O_3$ (calculated value %: C, 67.47; H, 5.91; N, 10.26. found value %: C, 67.30; H, 5.99; N, 10.34).

$^1$HNMR (DMSO-$d_6$): δ10.01 (s, 1H, CONH), 8.18-6.77, (6H, aromatic ring-H), 4.17-4.16 (2H, piperazine-H), 3.87 (m, 5H, O—$CH_2$,) 3.60-3.78 (2H, piperazine-H), 3.20-3.58 (m, 6H), 2.75 (t, J=8 Hz, 2H), 2.52 (t, J=8 Hz, 2H) 1.71-1.85 (m, 4H)

MS: m/z 409

Example 36

IV-3 Preparation of 6-[4-(4-(3-(6-fluoro-benzisoxazolyl))-1-piperazinyl)-n-butoxy]-(1H)-indole 6-hydroxyindole and 3-(1-(4-chlorobutyl)-4-piperidinyl)-6-fluoro-benzisoxazole are used as starting materials and react according to step 4 in the method of preparation of IV-1 to obtain 6-[4-(4-(3-(6-fluoro-benzisoxazoly))-1-piperazinyl)-n-butoxy]-(1H)-indole.

Element analysis: $C_2H_{24}FN_3O_2$ (calculated value %: C, 70.21; H, 6.15; N, 10.68. found value %: C, 70.25; H, 6.17; N, 10.61).

$^1$HNMR (DMSO-$d_6$): 8.23-6.77, (6H, aromatic ring-H), 4.15-4.19 (2H, piperazine-H), 3.87 (m, 5H, O—$CH_2$,) 3.60-3.72 (2H, piperazine-H), 3.20-3.58 (m, 6H), 2.75 (t, J=8 Hz, 2H), 2.52 (t, J=8 Hz, 2H) 1.71-1.85 (m, 4H)

MS: m/z 393

Example 37

IV-4 Preparation of 6-[4-(4-(3-(6-fluoro-benzisoxazolyl))-1-piperazinyl)-n-butoxy]-(1H)-benzimidazole 1) 3-hydroxy-o-phenylenediamine (1.24 g, 10 mmol) is added to 10 ml of formic acid and react at reflux for 2 hours, then most of formic acid is removed by evaporation. The residue is adjusted to pH=7 with saturated $NaHCO_3$ solution and extracted with ethyl acetate (30 ml×3). The extracting solution is washed with saturated saline, dried over anhydrous magnesium sulfate and filtered. The filtrate is evaporated and the residue is purified by column chromatography using neutral alumina to obtain 600 mg of 6-hydroxybenzimidazole.

6-hydroxybenzimidazole and 1-(4-chlorobutyl)-4-piperidinyl)-6-fluoro-benzisoxazole are used as starting materials and react according to step 4 in the method of preparation of IV-1 to obtain 6-[4-(4-(3-(6-fluoro-benzisoxazolyl))-1-piperazinyl)-n-butoxy]-(1H)-benzimidazole, with a yield of 75%.

Element analysis: $C_{23}H_{23}FN_4O_2$ (calculated value %: C, 66.99; H, 5.88; N, 14.20. found value %: C, 66.73; H, 5.83; N, 13.99).

$^1$HNMR (DMSO-$d_6$): 8.17-6.49, (6H, aromatic ring-H), 4.18-4.19 (2H, piperazine-H), 3.86 (m, 5H, O—$CH_2$,) 3.66-3.68 (2H, piperazine-H), 3.25-3.54 (m, 5H), 2.79 (t, J=8 Hz, 2H), 2.42 (t, J=8 Hz, 2H) 1.71-1.90 (m, 4H)

MS: m/z 394

Example 38

IV-5 Preparation of 6-[4-(4-(3-(6-fluoro-benzisoxazolyl))-1-piperazinyl)-n-butoxy]-(1H)-indazole 6-aminoindazole (2.66 g, 20 mmol) is added to 20% of dilute sulfuric acid and the reaction is performed under microwave radiation at 170° C. for 1 hour using microwave powder of 600 watt, and then terminated. The reaction solution is cooled, adjusted to pH=7 with 5% NaOH and stirred for 10 minutes to precipitated a deposit, which is recrystallized in water to obtain 1.5 g of 6-hydroxyindazole, with a yield of 51%.

6-hydroxyindazole and 3-(1-(4-chlorobutyl)-4-piperidinyl)-6-fluoro-benzisoxazole are used as starting materials and react according to step 4 in the method of preparation of IV-1 to obtain 6-[4-(4-(3-(6-fluoro-benzisoxazolyl))-1-piperazinyl)-n-butoxy]-(1H)-indazole, with a yield of 62%.

Element analysis: $C_{23}H_{23}FN_4O_2$ (calculated value %: C, 66.99; H, 5.88; N, 14.20. found value %: C, 66.71; H, 5.80; N, 13.89).

$^1$HNMR (DMSO-$d_6$): 8.21-6.49, (6H, aromatic ring-H), 4.18-4.19 (2H, piperazine-H), 3.87 (m, 5H, O—$CH_2$,) 3.66-3.75 (2H, piperazine-H), 3.25-3.54 (m, 5H), 2.79 (t, J=8 Hz, 2H), 2.42 (t, J=8 Hz, 2H) 1.71-1.90 (m, 4H)

MS: m/z 394

Example 39

IV-6 Preparation of 6-[4-(4-(3-(6-fluoro-benzisoxazolyl))-1-piperazinyl)-n-butoxy]-(1H)-benzo(1,2,3)triazole 1) To a solution of 3-nitro-4-aminophenol (4.6 g, 30 mmol) in methanol is added 500 mg of Pd/C. A hydrogenation reaction is performed at room temperature for 2 hours and then terminated. The Pd/C is removed by filtration to obtain 4.1 g of 3-hydroxy-o-phenylenediamine, with a yield of 95%.

2) To a solution of 0.2N HCl is added 3-hydroxy-o-phenylenediamine (1.0 g, 8 mmol), and then added slowly 600 mg of $NaNO_2$ solid. The mixture is stirred at room temperature for 1.5 hours after completion of addition, and then terminated. The reaction solution is extracted with ethyl acetate (30 ml×2) and the extracting solution is backwashed with 15% HCl (20 ml×2). The organic layer is dried, filtered and evaporated to dryness to obtain 6-hydroxy-(1H)-benzo(1,2,3)triazole.

3) 6-hydroxy-(1H)-benzo(1,2,3)triazole and 3-(1-(4-chlorobutyl)-4-piperidinyl)-6-fluoro-benzisoxazole are used as starting materials and react according to step 4 in the method of preparation of IV-1 to obtain 6-[4-(4-(3-(6-fluoro-benzisoxazolyl))-1-piperazinyl)-n-butoxy]-(1H)-benzo(1,3)triazole, with a yield of 70%

Element analysis: $C_{21}H_{22}FN_5O_2$ (calculated value %: C, 63.78; H, 5.61; N, 17.71. found value %: C, 64.01; H, 5.63; N, 17.78).

$^1$HNMR (DMSO-$d_6$): 8.21-6.49, (6H, aromatic ring-H), 4.18-4.19 (2H, piperazine-H), 3.87 (m, 5H, O—$CH_2$,) 3.66-3.75 (2H, piperazine-H), 3.25-3.54 (m, 6H), 2.79 (t, J=8 Hz, 2H), 2.42 (t, J=8 Hz, 2H) 1.71-1.90 (m, 4H)

MS: m/z 395

Example 40

IV-7 Preparation of 7-[4-(4-(3-(6-fluoro-benzisoxazolyl))-1-piperidinyl)-n-butoxy)-2(1H)-quinolinone 7-hydroxy-2(1H)-quinolinone and 3-(1-(4-chlorobutyl)-4-piperidinyl)-6-fluoro-benzisoxazole are used as starting materials and react according to step 4 in the method of preparation of IV-1 to obtain 7-[4-(4-(3-(6-fluoro-benzisoxazolyl))-1-piperidinyl)-n-butoxy)-2(1H)-quinolinone, with a yield of 52%.

Element analysis: $C_{24}H_{24}FN_3O_3$ (calculated value %: C, 68.39; H, 5.74; N, 9.97. found value %: C, 68.35; H, 5.95; N, 10.02.

$^1$HNMR (DMSO-$d_6$): δ10.03 (s, 1H, CONH), 8.16-6.77, (6H, aromatic ring-H), 4.11-4.16 (2H, piperazine-H), 3.81 (m, 5H, O—$CH_2$,) 3.65-3.78 (2H, piperazine-H), 3.25-3.58 (m, 6H), 2.75 (t, J=8 Hz, 2H), 2.52 (t, J=8 Hz, 2H) 1.71-1.85 (m, 4H)

MS: m/z 421

Example 41

IV-8 Preparation of 7-[4-(4-(3-(6-fluoro-benzisoxazolyl))-1-piperidinyl)-n-butoxy)-2H-benzo [b][1,4]oxazine-3(4H)-one 7-hydroxy-2H-benzo[b][1,4]oxazine-3(4H)-one and 3-(1-(4-chlorobutyl)-4-piperidinyl)-6-fluoro-benzisoxazole are used as starting materials and react according to step 4 in the method of preparation of IV-1 to obtain 7-[4-(4-(3-(6-fluoro-benzisoxazolyl))-1-piperidinyl)-n-butoxy)-2H-benzo[b][1,4]oxazine-3(4H)-one, with a yield of 51%.

Element analysis: $C_{23}H_{24}FN_3O_4$ (calculated value %: C, 64.93; H, 5.69; N, 9.88. found value %: C, 64.91; H, 5.66; N, 9.81).

$^1$HNMR (DMSO-$d_6$): δ10.03 (s, 1H, CONH), 8.16-6.77, (6H, aromatic ring-H), 4.11-4.16 (2H, piperazine-H), 3.81 (m, 5H, O—$CH_2$,) 3.65-3.78 (2H, piperazine-H), 3.25-3.58 (m, 6H), 2.75 (t, J=8 Hz, 2H), 2.52 (t, J=8 Hz, 2H) 1.71-1.85 (m, 4H)

MS: m/z 425

Example 42

IV-9 Preparation of 7-[4-(4-(3-(6-fluoro-benzisoxazolyl))-1-piperidinyl)-n-butoxy)-3-methyl-2(1H)-quinolinone 7-hydroxy-3-methyl-2(1H)-quinolinone and 3-(1-(4-chlorobutyl)-4-piperidinyl)-6-fluoro-benzisoxazole are used as starting materials and react according to step 4 in the method of preparation of IV-1 to obtain 7-[4-(4-(3-(6-fluoro-benzisoxazolyl))-1-piperidinyl)-n-butoxy)-3-methyl-2(1H)-quinolinone, with a yield of 73%.

Element analysis: $C_{25}H_{26}FN_3O_3$ (calculated value %: C, 68.95; H, 6.02; N, 9.65. found value %: C, 68.99; H, 6.04; N, 9.67).

$^1$HNMR (DMSO-$d_6$): δ10.08 (s, 1H, CONH), 8.13-6.77, (6H, aromatic ring-H), 4.25-4.16 (2H, piperazine-H), 3.77 (m, 5H, O—$CH_2$,) 3.65-3.0 (2H, piperazine-H), 3.25-3.58 (m, 6H), 2.75 (t, J=8 Hz, 2H), 2.52 (t, J=8 Hz, 2H) 1.71-1.85 (m, 7H)

MS: m/z 435

Example 43

IV-10 Preparation of 7-[4-(4-(3-(6-fluoro-benzisoxazolyl))-1-piperidinyl)-n-butoxy)-4-methyl-2(1H)-quinolinone 7-hydroxy-4-methyl-2(1H)-quinolinone and 3-(1-(4-chlorobutyl)-4-piperidinyl)-6-fluoro-benzisoxazole are used as starting materials and react according to step 4 in the method of preparation of IV-1 to obtain 7-[4-(4-(3-(6-fluoro-benzisoxazolyl))-1-piperidinyl)-n-butoxy)-3-methyl-2(1H)-quinolinone, with a yield of 73%.

Element analysis: $C_{25}H_{26}FN_3O_3$ (calculated value %: C, 68.95; H, 6.02; N, 9.65. found value %: C, 68.90; H, 6.01; N, 9.60).

$^1$HNMR (DMSO-$d_6$): δ10.08 (s, 1H, CONH), 8.11-6.77, (6H, aromatic ring-H), 4.24-4.16 (2H, piperazine-H), 3.77 (m, 5H, O—$CH_2$,) 3.64-3.0 (2H, piperazine-H), 3.21-3.58 (m, 6H), 2.74 (t, J=8 Hz, 2H), 2.52 (t, J=8 Hz, 2H) 1.71-1.85 (m, 7H)

MS: m/z 435

Example 44

| tablets: | the derivative of the present invention | 25 mg |
|---|---|---|
| | sucrose | 155 mg |
| | corn starch | 65 mg |
| | magnesium stearate | 5 mg | formulation method: an active ingredient is blended with sucrose and corn starch, and to the blend is added water for wetting. The mixture is stirred evenly, dried, ground, sieved, and added with magnesium stearate, and mixed evenly and compressed into a tablet. Each tablet is weighted 250 mg and contains 25 mg of an active ingredient.

Example 45

| Injections: | the derivative of the present invention | 10 mg |
|---|---|---|
| | Water for injection | 90 mg | formulation method: an active ingredient is dissolved into water for injection and mixed evenly and filtered. The obtained solution is dispensed into an ampoule under aseptic condition with each ampoule containing an amount of 10 mg with 1 mg/ampoule of an active ingredient.

Example 46

A Dopamine $D_2$ Receptor-Binding Assay

Test Materials:

An isotope ligand for $D_2$ receptor: [$^3$H]Spiperone (77.0 Ci/mmol); (+)Butaclamol; GF/C glass fiber media; a liposoluble scintillation solution; and the $D_2$ receptor protein expressed by sf9 cells.

Testing Method:

A binding assay of a film product of CHO-h$D_{2L}$ cells and [$^3$H]Spiperone is conducted in a 250 μl of 50 mM of Tris-HCl 250 buffer (Ph=7.4) solution comprising 100 mM of NaCl, 1 mM of $MgCl_2$ and 1% of DMSO. A sample in duplicate containing compounds to be tested, 0.4 nM of [$^3$H]Spiperone and 12 ug of protein is maintained at room temperature for 120 minutes. The bound radioactive ligand is separated by flash filtration under reduced pressure using Whatman GF/B glass fiber filter pre-treated with 0.3% polyethylenelmine, and radioactivity maintained on the filter is measured using liquid scintillation spectrophotometry. The title compounds in the following examples are tested using the above test, which comprises first of all testing competitive inhibition rate of each compound at a concentration of 10 umol/L to binding of [$^3$H]Spiperone to $D_2$ receptor through a rough screening; and compounds having inhibition rate higher than 95% are subjected to receptor binding assay under a series of concentrations to determine a half-inhibitory concentration ($IC_{50}$, the concentration of a compound needed for inhibiting binding of 50% [$^3$H]Spiperone to $D_2$ receptor). Two tubes under each concentration are measured, and each compound is subjected to two independent tests. The test results shows that all compounds under 10 uM exhibit occupancy of $D_2$ receptor of higher than 95%, and all different compounds have $IC_{50}$ values less or equal to 500 nM (see the following Table 1). The preferable solutions of the compound of the present invention has a $IC_{50}$ value not greater than 100 nM, more preferably not greater than 500 nM, even more preferably not greater than 25 nM, and the most preferably not greater than 10 nM.

TABLE 1

Affinity of part of compounds to $D_2$ receptor

| No. | $IC_{50}$ (nM) |
|---|---|
| I-1 | 25.7 |
| I-2 | 56.8 |
| I-3 | 99.3 |
| I-4 | 10.2 |
| I-5 | 53.6 |
| I-7 | 289.6 |
| I-8 | 156.8 |
| I-9 | 25.0 |
| I-11 | 77.8 |
| I-12 | 10.2 |
| II-1 | 5.66 |
| II-2 | 16.2 |
| II-3 | 202 |
| II-4 | 23.6 |
| II-5 | 15.8 |
| II-6 | 277 |
| II-7 | 12.6 |
| II-8 | 23.8 |
| II-9 | 78.8 |
| II-10 | 45.6 |
| III-1 | 5.23 |
| III-2 | 76.8 |
| III-4 | 17.9 |
| III-5 | 15.8 |
| III-6 | 15.0 |
| III-7 | 168.3 |

TABLE 1-continued

Affinity of part of compounds to $D_2$ receptor

| No. | $IC_{50}$ (nM) |
|---|---|
| IV-1 | 38.9 |
| IV-3 | 12.3 |
| IV-4 | 15.3 |

Example 47

An Antagonistic Test of $D_2$ Receptor

1. Test Materials:

CHO cell that stably expresses $rD_2R$; Forskolin, IBMX, Dopamine, and Haloperidol are purchased from Sigma; and the rest reagents are purchased from Shanghai Chemical Company of China National Medicine Corp.

Figure 2:
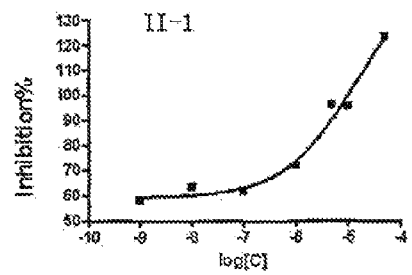
FIG. 2 represents a curve demonstrating an affinity of compound II-1 for dopamine $D_2$ receptor.
Figure 3:
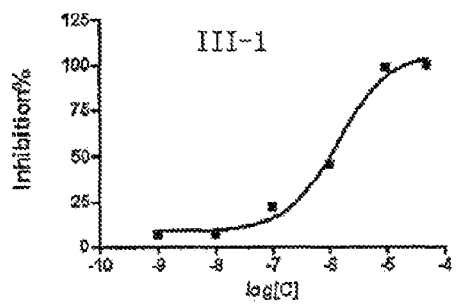
FIG. 3 represents a curve demonstrating an affinity of compound III-1 for dopamine $D_2$ receptor.

2. Test Methods:

CHO-$rD_2$ cell is seeded on a 96-well plate at a concentration of 30,000 cells/well, and cultured overnight; each medicine is dissolved in a serum-free F12 culture media containing 100 μM of IBMX, and is added to the above cell for preculturing 30 minutes at 37° C.; thereafter a serum-free $F_{12}$ culture media containing 10 μM of Forskolin and 10 μM of Dopamine is added and react for 8 minutes, and then 100 μl of pre-cooled 1M $HClO_4$ is added to terminate the reaction. The reaction solution is allowed to stand on ice for 40 minutes, and thereto 20 μl of 2M $K_2CO_3$ is added to neutralize the reaction solution. The reaction solution is centrifuged at 3,000 rpm for 15 minutes at 4° C., and a $KClO_4$ deposit is discarded. An amount of supernatant is diluted in 0.05M of acetic acid buffer, and the amount of generated cAMP is measured with radioimmunoassay method. The [$^{125}$I]cAMP radioimmunoassay kit is purchased from Nuclear Medicine Testing Center of Shanghai University of Traditional Chinese Medicine. See the kit's instructions for detailed steps. Two tubes under each concentration of each compound are measured, and each compound is subjected to two independent tests. The test results are shown in FIGS. 1-3.

The ordinate of the dose-effect curve represents a reduced percentage of the amount of generated cAMP through antagonist of DA by the compound.

TABLE 2

An antagonistic result of part of compounds

| No. | $IC_{50}(\mu M)$ |
|---|---|
| Haloperidol | 0.346 |
| II-1 | 3.38 |
| III-1 | 56.4 |
| IV-1 | 198 |

Example 48

A [$^3$H]Adenosine Uptake Test for $D_2$ Inherent Agitation Activity

Figure 4:
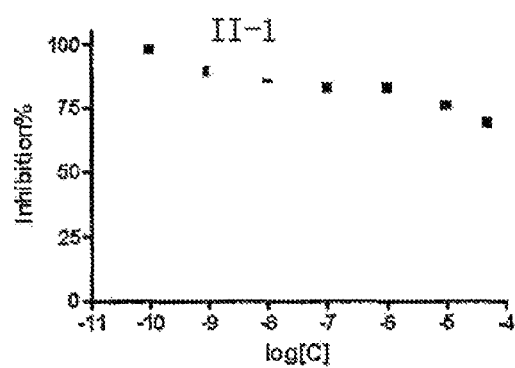
FIG. 4 represents a curve demonstrating partial agonistic activity of compound II-1 on dopamine $D_2$ receptor.

Removing serum from cells by washing with 200 μl of a serum-free culture medium twice, and adding 90 μl of a serum-free culture medium to each well. Incubating the flat plate for 2-3 hours. 10μ of a serum-containing culture medium, which is used as a positive control, carrier (a serum-free culture medium), negative control (an antagonist) or the tested compounds in a serum-free culture medium and standard (10 μl of a 10 uM solution having a final concentration of 1 uM) are added to each well. The flat plate is returned to an incubator. After 18 hours, adding [$^3$H]adenosine (0.5 μCi/well) to 10 μl of a serum-free culture medium, and the flat plate is returned to the incubator. After 4 hours, adding trypsin (0.25%) (100 μl/well), and the flat plate is returned to the incubator again. After 1 hour, terminating the test by flash filtration using Whatman GF/B glass fiber filter. For example, using Brandel MLR-96T cell collector, washing filter with 500 ml of 50 mM Tris-HCl pH7.0 buffer solution, and using Wallac 1205 Betaplate liquid scintillation counter to evaluate the radioactivity maintained on the filter (half-effective amount). The inherent activity is defined as to deduct the serum-free culture medium from the total uptake amount (1 μM Quinpirole), and compare the tested compounds with 1 μM Quinpirole that is classified as having 100% inherent activity. All tests are conducted preferably in triplicate, wherein each medicine occupies a complete column in each flat plate. The compound of the present invention exhibits preferably at least 1%-90% inherent activity, more preferably at least 10%-90% activity, more preferably at least 10%-80% activity, more preferably at least 20%-60% inherent activity, more preferably at least 30%-50% inherent activity. The test result is shown in FIG. 4.

Example 49

A Test of In Vivo Anti-Schizophrenia Activity of Compound II-1

1. Test Materials (1) Formulation and Dosage of a Test Reagent and a Solution Thereof Apomorphine: apomorphine is dissolved in 0.1% ascorbic acid to form a solution having a dosage of 10 mg/kg.

Aripiprazole is dissolved in physiological saline to form a solution having a dosage of 5 mg/kg, and subjected to ultra-sonication for dissolving.

Risperidone is dissolved in physiological saline to form a solution having a dosage of 0.25 mg/kg.

Compound II-1 is formulated to 20 mg/kg, and is formulated in situ for use.

(2) Test Animals and Grouping

Female KM mice, 18-22 g, are randomly divided into a solvent control group, a model control group, a positive control group, and various treatment groups of the tested medicines. Groups for behavior observation test contain 5 mice each group, and groups for activity observation test contain 4 mice each group.

2. Test Methods (1) Administration in mice: each group of mice is administrated with 0.1 ml/10 g of the various tested medicines by oral gavage.

(2) Modeling in Mice 30 minutes after the administration of the tested medicine, the mice are intraperitoneally injected with a 10 mg/kg solution of apomorphine at 0.1 ml/10 g body weight of the mice.

(3) Testing 3.1 Observation of Stereotyped Behavior

The mice are administrated with apomorphine. Thereafter, observing whether the mice have stereotyped behaviors such as tail elevation, smelling, nibbling, jumping, wall-climbing, head elevation, etc. at the first 30 sec. from the 5th, 10th, 15th, 20th, 25th, and 30th minutes, and scoring according to the following standard: those without the above behaviors in the 30 sec of the observation belong to level 0; those having the above behaviors not in consecutive and at a moderate degree in the 30 sec of the observation belong to level 1; and those having the above behaviors in consecutive and at a strong degree in the 30 sec of the observation belong to level 2.

3.2 Observation of the Number of Activities of the Mice

After the administration of apomorphine, the mice are immediately put into a case for free moving, allowed to adapt to the environment for 5 minutes first of all, and then is recorded their number of activities at 0-5, 5-10, 10-15, 15-20, 20-25, 25-30 minutes.

(4) Treatment of the Test Results 4.1 The Observation Test of Stereotyped Behavior The stereotyped behavior numbers of the mice in various groups at six time points are statistically analyzed to calculate an average number of each mouse, and the result is denoted by mean±SD.

4.2 The Observation Test of the Number of Activities of the Mice

The total numbers of activities of the mice in various groups in each time interval are statistically analyzed to calculate an average value of each mouse, and the result is denoted by mean±SD.

(5) The Statistical Method

The test result of stereotyped behavior is statistically analyzed using a LSD method; and observation result of the numbers of activities of the mice is statistically analyzed with repeated-measures analysis of variance and Q-test.

3. Test Results

Figure 5:
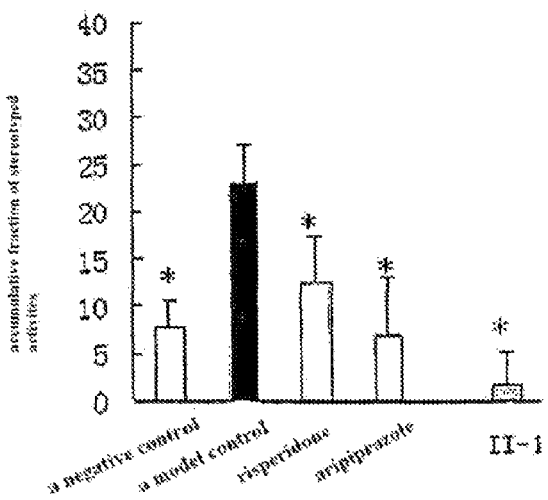
FIG. 5 and FIG. 6 represent an effect of compound II-1 on schizophrenia behaviors in mice induced by apomorphine.
Figure 6:
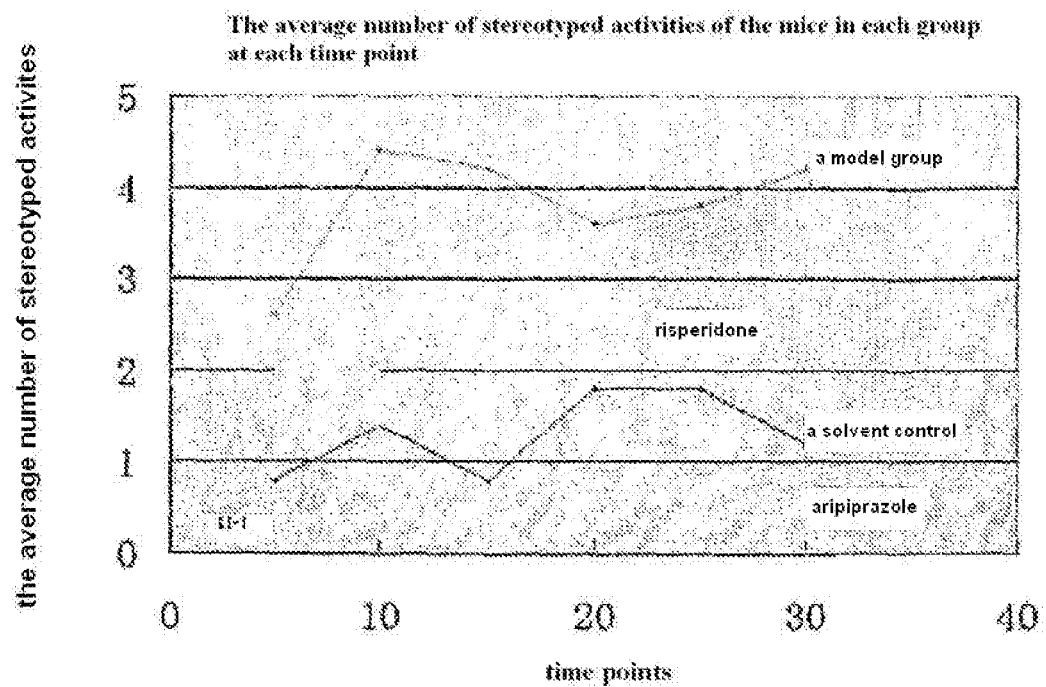

The result of observation test of stereotyped behavior: see FIGS. 5 and 6.

The above tests show the followings:

a. As compared with the mice in the negative control group, the group that has been modeled with apomorphine has an obviously increased score of stereotyped activity, suggesting that apomorphine causes schizophrenia in mice.

b. As compared with the model group, the number of stereotyped activities of mice is reduced significantly by risperidone, aripiprazol, and compound II-1, suggesting that the compound has a certain anti-schizophrenia effect.

Example 50

A Study on Acute Toxicity of II-1

Using a Bliss method shows that the mice with a single administration of compound II-1 by oral gavage have a $LD_{50}$ of greater than 2000 mg/kg. An acute toxicity of the compound II-1 is far more less than that of risperidone (83.2 mg/kg) and comparable to that of aripiprazole (1400 mg/kg) and ziprasidone (1600 mg/kg).

Example 51

Bacterial Reverse Mutation Test of II-1

Strains: histidine auxotroph mutant of mouse salmonella $TA_{97}$, $TA_{98}$, $TA_{100}$ and $TA_{102}$.

Results: the test consists of two parts, i.e., $-S_9$ and $+S_9$. A bacteriostatic action is showed at a dose of 5000 μg per dish for $TA_{98}$ in the test system without $S_9$ and for $TA_{97}$ in the test system containing $S_9$. No bacteriostatic actions to all the strains are observed at all other doses, and the growth background is good. All the tested doses, in the test system with or without $S_9$, do not cause any significant increase in the number of revertant colonies and Ames test is negative.

The invention claimed is:

1. An aralkyl substituted piperidine or piperazine derivative, which is a compound represented by following formula (1) or a free base or a pharmaceutically acceptable salt of said compound:

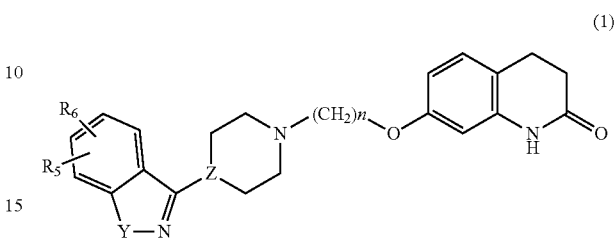

wherein:
Z is CH or N;
Y is O or S;
n is an integer of 3 or 4; and
$R_5$ or $R_6$ represents one of hydrogen, $C_1$-$C_4$ alkyl, hydroxy, $C_1$-$C_4$ alkoxy, halogen or acetonitrile;
wherein the alkyl moiety in the $C_1$-$C_4$ alkyl and $C_1$-$C_4$ alkoxy is optionally substituted with 1-3 fluorine atom(s).

2. The aralkyl substituted piperidine or piperazine derivative according to claim 1, wherein said salt is a salt containing a pharmaceutically acceptable anion.

3. The aralkyl substituted piperidine or piperazine derivative according to claim 1, wherein said salt is hydrochloride, hydrobromide, sulfate, trifluoroacetate or methanesulfonate.

4. An aralkyl substituted piperidine or piperazine derivative selected from:
I-1 7-[4-(4-(3-(6-chloro-benzisoxazolyl))-1-piperazinyl)-n-butoxy]-3,4-dihydro-2(1H)-quinolinone,
I-2 7-[4-(4-(3-(5-chloro-benzisoxazolyl))-1-piperazinyl)-n-butoxy]-3,4-dihydro-2(1H)-quinolinone,
I-3 7-[4-(4-(3-(benzisoxazolyl))-1-piperadinyl)-n-butoxy]-3,4-dihydro-2(1H)-quinolinone,
I-4 7-[4-(4-(3-(6-fluoro-benzisoxazolyl))-1-piperazinyl)-n-butoxy]-3,4-dihydro-2(1H)-quinolinone,
I-5 7-[4-(4-(3-(6-trifluoromethyl-benzisoxazolyl))-1-piperazinyl)-n-butoxy]-3,4-dihydro-2(1H)-quinolinone,
I-6 7-[4-(4-(3-(6-methyl-benzisoxazolyl))-1-piperazinyl)-n-butoxy]-3,4-dihydro-2(1H)-quinolinone,
I-7 7-[4-(4-(3-(5-methyl-benzisoxazolyl))1-piperazinyl)-n-butoxy]-3,4-dihydro-2(1H)-quinolinone,
I-8 7-[4-(4-(3-(6-hydroxy-benzisoxazolyl))-1-piperazinyl)-n-butoxy]-3,4-dihydro-2(1H)-quinolinone,
I-9 7-[4-(4-(3-(5-methoxy-benzisoxazolyl))-1-piperazinyl)-n-butoxy]-3,4-dihydro-2(1H)-quinolinone,
I-10 7-[4-(4-(3-(5-cyano-benzisoxazolyl))-1-piperazinyl)-n-butoxy]-3,4-dihydro-2(1H)-quinolinone,
I-11 7-[4-(4-(3-(5-bromo-benzisoxazolyl))1-piperazinyl)-n-butoxy]-3,4-dihydro-2(1H)-quinolinone,
I-12 7-[4-(4-(3-(7-bromo-6-methoxy-benzisoxazolyl))-1-piperazinyl)-n-butoxy]-3,4-dihydro-2(1H)-quinolinone,
II-1 7-[4-(4 (3-((6-fluoro-benzisoxazolyl))-1-piperazinyl)-n-butoxy]-3,4-dihydro-2(1H)-quinolinone,
II-2 7-[3-(4-(3-(6-fluoro-benzisoxazolyl))-1-piperidinyl)-n-propoxy]-3,4-dihydro-2(1H)-quinolinone,
II-3 7-[2-(4-(3-(6-fluoro-benzisoxazolyl))-1-piperidinyl)-ethoxy]-3,4-dihydro-2(1H)-quinolinone, II-4 7-[2-(4-(3-benzisoxazolyl)-1-piperidinyl)-ethoxy]-3,4-dihydro-2(1H)-quinolinone,
II-5 7-[4-(4-(3-(6-chloro-benzisoxazolyl))-1-piperidinyl)-n-butoxy]-3,4-dihydro-2(1H)-quinolinone,
II-6 7-[4-(4-(3-(5-methoxy-benzisoxazolyl))-1-piperidinyl)-n-butoxy]-3,4-dihydro-2(1H)-quinolinone,
II-7 7-[4-(4-(3-(5-fluoro-benzisoxazolyl))-1-piperidinyl)-n-butoxy]-3,4-dihydro-2(1H)-quinolinone,
II-8 7-[4-(4-(3-(5,6-dimethoxy-benzisoxazolyl))1-piperidinyl)-n-butoxy]-3,4-dihydro-2(1H)-quinolinone,
II-9) 7-[4-(4-(3-(5-hydroxy-benzisoxazolyl))-1-piperidinyl)-n-butoxy]-3,4-dihydro-2(1H)-quinolinone,
II-10 7-[4-(4-(3-(5,6-dihydroxy-benzisoxazolyl))-1-piperidinyl)-n-butoxy]-3,4-dihydro-2(1H)-quinolinone,
II-11 E-7-[4-(4-(3-(6-fluoro-benzisoxazolyl))1-piperidinyl)-2-butenyloxy]-3,4-dihydro-2(1H)-quinolinone,
II-12 Z-7-[4-(4-(3-(6-fluoro-benzisoxazolyl))-1-piperidinyl)-2-butenyloxy]-3,4-dihydro-2(1H)-quinolinone,
II-13 7-(((1R,2S)-2-(4-(3-(6-fluoro-benzisoxazolyl))-1-piperidinyl)methyl)cyclohexyl)methoxy)-3,4-dihydro-2(1H)-quinolinone,
II-14 7-(((1R,2R)-2-(4-(3-(6-fluoro-benzisoxazolyl))-1-piperidinyl)methylcyclohexyl)methoxy)-3,4-dihydro-2(1H)-quinolinone,
III-1 7-[4-(4-(3-(1,2-benzisothiazolyl))-1-piperazinyl-n-butoxy]-3,4-dihydro-2(1H)-quinolinone,
III-2 7-[3-(4-(3-(1,2-benzisothiazolyl))-1-piperazinyl)-n-propoxy]-3,4-dihydro-2(1H)-quinolinone,
III-3 7-[2-(4-(3-(1,2-benzisothiazolyl))-1-piperazinyl)-ethoxy]-3,4-dihydro-2(1H)-quinolinone,
III-4 7-[4-(4-(3-(6-methoxy-1,2-benzisothiazolyl))-1-piperazinyl)-n-butoxy]-3,4-dihydro-2(1H)-quinolinone,
III-5 7-[4-(4-(3-(7-methoxy-1,2-benzisothiazolyl))-1-piperazinyl)-n-butoxy]-3,4-dihydro-2(1H)-quinolinone,
III-6 7-[4-(4-(3-(5-methoxy-1,2-benzisothiazolyl))-1-piperazinyl)-n-butoxy]-3,4-dihydro-2(1H)-quinolinone,
III-7 7-[4-(4-(3-(4-methoxy-1,2-benzisothiazolyl))-1-piperazinyl)-n-butoxy]-3,4-dihydro-2(1H)-quinolinone,
IV-1 6-[4-(4-(3-(6-fluoro-benzisoxazolyl))-1-piperidinyl)-n-butoxy)-indolin-2-one,
IV-2 5-[4-(4-(3-(6-fluoro-benzisoxazolyl))-1-piperidinyl)-n-butoxy)-2(3H)-benzoxazolone,
IV-4 6-[4-(4-(3-(6-fluoro-benzisoxazolyl))-1-piperazinyl)-n-butoxy]-(1H)-benzimidazole,
IV-5 6-[4-(4-(3-(6-fluoro-benzisoxazolyl))-1-piperazinyl)-n-butoxy]-(1H)-indazole,
IV-6 6-[4-(4-(3-(6-fluoro-benzisoxazolyl))-1-piperazinyl)-n-butoxy]-(1H)-benzo(1,2,3)triazole,
IV-7 7-[4-(4-(3-(6-fluoro-benzisoxazolyl))-1-piperidinyl)-n-butoxy)-2(1H)-quinolinone,
IV-8 7-[4-(4-(3-(6-fluoro-benzisoxazolyl))-1-piperidinyl)-n-butoxy)-2H-benzo[b][1,4]oxazine-3(4H)-one,
IV-9 7-[4-(4-(3-(6-fluoro-benzisoxazolyl))-1-piperidinyl)-n-butoxy)-3-methyl-2(1H)-quinolinone,
IV-10 7-(4-(4-(3-(6-fluoro-benzisoxazolyl))-1-piperidinyl)-n-butoxy)-4-methyl-2(1H)-quinolinone, or
its free base or a pharmaceutically acceptable salt thereof.
5. A composition for treatment of schizophrenia, said composition comprises a therapeutically effective amount of the compound of claim 1 or a free base or a pharmaceutically acceptable salt thereof and a pharmaceutically acceptable carrier.
6. A method of manufacturing a medicament for treatment of schizophrenia, the method comprising combining a therapeutically effective amount of the compound according to claim 1 or a free base or a pharmaceutically acceptable salt thereof and a pharmaceutically acceptable carrier.
7. A composition for treatment of schizophrenia, said composition comprises a therapeutically effective amount of the compound of claim 4 or a free base or a pharmaceutically acceptable salt thereof and a pharmaceutically acceptable carrier.
8. A method of manufacturing a medicament for treatment of schizophrenia, the method comprising combining a therapeutically effective amount of the compound according to claim 4 or a free base or a pharmaceutically acceptable salt thereof and a pharmaceutically acceptable carrier.
9. An aralkyl substituted piperidine or piperazine derivative, which is a compound represented by following formula (1) or a free base or a pharmaceutically acceptable salt of said compound:

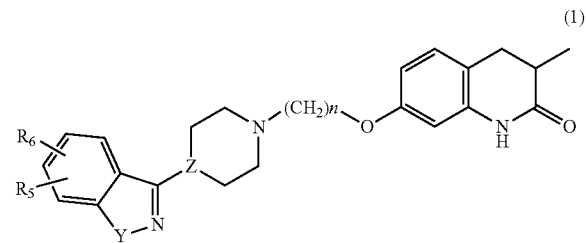

wherein:
Z is CH or N;
Y is O or S;
n is an integer of 3 or 4; and
$R_5$ or $R_6$ represents one of hydrogen, $C_1$-$C_4$ alkyl, hydroxy, $C_1$-$C_4$ alkoxy, halogen or acetonitrile;
wherein the alkyl moiety in the $C_1$-$C_4$ alkyl and $C_1$-$C_4$ alkoxy is optionally substituted with 1-3 fluorine atom(s).
10. The aralkyl substituted piperidine or piperazine derivative according to claim 9, wherein said salt is a salt containing a pharmaceutically acceptable anion.
11. The aralkyl substituted piperidine or piperazine derivative according to claim 9, wherein said salt is hydrochloride, hydrobromide, sulfate, trifluoroacetate or methanesulfonate.
12. A composition for treatment of schizophrenia, said composition comprises a therapeutically effective amount of the compound of claim 9 or a free base or a pharmaceutically acceptable salt thereof and a pharmaceutically acceptable carrier.
13. A method of manufacturing a medicament for treatment of schizophrenia, the method comprising combining a therapeutically effective amount of the compound according to claim 9 or a free base or a pharmaceutically acceptable salt thereof and a pharmaceutically acceptable carrier.

* * * * *